(12) United States Patent
Lisanti et al.

(10) Patent No.: US 12,006,553 B2
(45) Date of Patent: Jun. 11, 2024

(54) COMPANION DIAGNOSTICS FOR MITOCHONDRIAL INHIBITORS

(71) Applicant: LUNELLA BIOTECH, INC., Ottawa (CA)

(72) Inventors: Michael P. Lisanti, Fulton, MD (US); Federica Sotgia, Fulton, MD (US)

(73) Assignee: LUNELLA BIOTECH, INC., Ontario (CA)

( * ) Notice: Subject to any disclaimer, the term of this patent is extended or adjusted under 35 U.S.C. 154(b) by 781 days.

(21) Appl. No.: 16/614,581

(22) PCT Filed: May 18, 2018

(86) PCT No.: PCT/US2018/033488
§ 371 (c)(1),
(2) Date: Nov. 18, 2019

(87) PCT Pub. No.: WO2018/213764
PCT Pub. Date: Nov. 22, 2018

(65) Prior Publication Data
US 2020/0255902 A1   Aug. 13, 2020

Related U.S. Application Data

(60) Provisional application No. 62/590,432, filed on Nov. 24, 2017, provisional application No. 62/576,287, filed on Oct. 24, 2017, provisional application No. 62/529,871, filed on Jul. 7, 2017, provisional application No. 62/524,829, filed on Jun. 26, 2017, provisional application No. 62/508,750, filed on May 19, 2017, provisional application No. 62/508,799, filed on May 19, 2017, provisional application No. 62/508,788, filed on May 19, 2017, provisional application No. 62/508,769, filed on May 19, 2017.

(30) Foreign Application Priority Data

Mar. 14, 2018 (WO) .............. PCT/US2018/022403

(51) Int. Cl.
*C12Q 1/6886* (2018.01)
*C12Q 1/6816* (2018.01)

(52) U.S. Cl.
CPC ......... *C12Q 1/6886* (2013.01); *C12Q 1/6816* (2013.01); *C12Q 2565/00* (2013.01); *C12Q 2600/106* (2013.01); *C12Q 2600/158* (2013.01)

(58) Field of Classification Search
None
See application file for complete search history.

(56) References Cited

U.S. PATENT DOCUMENTS

| | | |
|---|---|---|
| 3,517,067 A | 6/1970 | Stern |
| 5,168,057 A | 12/1992 | Oh et al. |
| 5,250,518 A | 10/1993 | Kobrehel et al. |
| 5,441,939 A | 8/1995 | Yang |
| 5,795,871 A | 8/1998 | Narita et al. |
| 5,837,696 A | 11/1998 | Golub et al. |
| 6,043,226 A | 3/2000 | Lundy et al. |
| 6,165,999 A | 12/2000 | Vu |
| 6,475,518 B1 | 11/2002 | Baumgart et al. |
| 6,858,598 B1 | 2/2005 | McKearn et al. |
| 7,405,227 B2 | 7/2008 | Kun et al. |
| 7,485,298 B2 | 2/2009 | Powell |
| 8,075,902 B2 | 12/2011 | Powell |
| 8,357,723 B2 | 1/2013 | Satyam |
| 8,741,853 B2 | 6/2014 | Steliou |
| 9,394,233 B2 | 7/2016 | Merino et al. |
| 9,622,982 B2 | 4/2017 | Bannister et al. |
| 9,675,578 B2 | 6/2017 | Desai et al. |
| 9,801,922 B2 | 10/2017 | Spitz et al. |
| 10,188,668 B2 | 1/2019 | Bannister et al. |
| 2001/0002404 A1 | 5/2001 | Webb |
| 2004/0029114 A1* | 2/2004 | Mack .................... C07K 14/47 435/325 |
| 2005/0002942 A1 | 1/2005 | Vlahov et al. |
| 2005/0209292 A1 | 9/2005 | Chuang et al. |
| 2005/0256081 A1 | 11/2005 | Peyman |
| 2006/0019256 A1* | 1/2006 | Clarke ................ G01N 33/574 435/6.14 |
| 2007/0048296 A1 | 3/2007 | Kajander et al. |
| 2007/0105937 A1 | 5/2007 | Pappolla et al. |
| 2008/0045589 A1 | 2/2008 | Kelley |
| 2008/0160007 A1 | 7/2008 | Powell |
| 2008/0241959 A1 | 10/2008 | Culic et al. |
| 2009/0311249 A1 | 12/2009 | Gianni et al. |

(Continued)

FOREIGN PATENT DOCUMENTS

| | | |
|---|---|---|
| EP | 0656422 | 6/1995 |
| EP | 0941998 | 9/2004 |

(Continued)

OTHER PUBLICATIONS

Tuttle et al. PLoS ONE. Jan. 2014. 9: e87325 (Year: 2014).*
Vogel et al. Nature Review Genet. Mar. 2012. 13(4): 227-232 (Year: 2012).*
Chen et al. Molecular & Cellular Proteomics. 2002. 1: 304-313 (Year: 2002).*
Klopocki et al Annual Reviews Genomics Human Genetics. 2011. 12: 53-72 (Year: 2011).*
Sutherland et al. Acta Oncologica. 1995. 34: 651-656 (Year: 1995).*
Al-Mulla et al. J Clin Pathol. 2003. 56: 210-217 (Year: 2003).*
Kirilyuk I.A. et al., Nitroxyl Antioxidant TPPA-TEMPO Increases the Efficacy of Antitumor Therapy on the Model of Transplantable Mouse Tumor, Bulletin of Experimental Biology and Medicine, vol. 150, No. 1, Apr. 26, 2010 ONCOLOGY, pp. 75-78.

(Continued)

*Primary Examiner* — Carla J Myers
(74) *Attorney, Agent, or Firm* — Nixon & Vanderhye, P.C.

(57) ABSTRACT

The present disclosure relates to methods of identifying patients that may be responsive to mitochondrial inhibitor therapies to target and eradicate cancer stem cells. Also described are diagnostic kits that may be used to identify patients responsive to mitochondrial inhibitor therapies.

9 Claims, 13 Drawing Sheets

(56) References Cited

U.S. PATENT DOCUMENTS

| | | | |
|---|---|---|---|
| 2010/0120679 A1 | 5/2010 | Xu et al. | |
| 2010/0202969 A1 | 8/2010 | Panyam et al. | |
| 2010/0285001 A1 | 11/2010 | Land et al. | |
| 2011/0008418 A1 | 1/2011 | Ko | |
| 2011/0268722 A1 | 11/2011 | Siegelin et al. | |
| 2012/0071465 A1 | 3/2012 | Clement et al. | |
| 2012/0141467 A1 | 6/2012 | Schneider | |
| 2014/0142056 A1 | 5/2014 | Shanmugam et al. | |
| 2014/0187611 A1 | 7/2014 | Auwerx et al. | |
| 2014/0296085 A1* | 10/2014 | Baker | G01N 33/57415 435/6.12 |
| 2014/0303085 A1 | 10/2014 | Wong et al. | |
| 2014/0364595 A1 | 12/2014 | Bapat et al. | |
| 2015/0079154 A1 | 3/2015 | Zender et al. | |
| 2015/0224169 A1 | 8/2015 | Bhatia et al. | |
| 2015/0224206 A1 | 8/2015 | Van | |
| 2015/0231069 A1 | 8/2015 | Modi | |
| 2015/0366884 A1 | 12/2015 | Schultz et al. | |
| 2016/0008332 A1 | 1/2016 | Haq et al. | |
| 2016/0032401 A1 | 2/2016 | Jain et al. | |
| 2016/0339106 A1 | 11/2016 | Shanta | |
| 2017/0014361 A1 | 1/2017 | Dhar | |
| 2017/0035832 A1 | 2/2017 | Liu et al. | |
| 2017/0095460 A1 | 4/2017 | Fathi et al. | |
| 2017/0224730 A1 | 8/2017 | Berenson | |
| 2017/0232008 A1 | 8/2017 | Zeicher | |
| 2018/0214472 A1 | 8/2018 | Bapat et al. | |

FOREIGN PATENT DOCUMENTS

| | | |
|---|---|---|
| JP | 2016-155679 | 9/2016 |
| WO | 1995015770 | 6/1995 |
| WO | 99/26582 | 6/1999 |
| WO | 01/51923 | 7/2001 |
| WO | 2010/111208 | 9/2010 |
| WO | 2010/121177 | 10/2010 |
| WO | WO 2011/031474 | 3/2011 |
| WO | WO 2012024612 | 2/2012 |
| WO | 2012/166700 | 12/2012 |
| WO | WO 2013019975 A1 | 2/2013 |
| WO | 2013/040206 | 3/2013 |
| WO | 2014/052305 | 4/2014 |
| WO | WO 2014/138338 A1 | 9/2014 |
| WO | 2015/191668 | 12/2015 |
| WO | 2016/027089 | 2/2016 |
| WO | 2016/059247 | 4/2016 |
| WO | 2017/024207 | 2/2017 |
| WO | 2018/027252 | 2/2018 |
| WO | 2018/136598 | 7/2018 |
| WO | 2018/136617 | 7/2018 |
| WO | 2018/195434 | 10/2018 |
| WO | 2018/195446 | 10/2018 |
| WO | 2018/202910 | 11/2018 |
| WO | 2018/213751 | 11/2018 |
| WO | 2018/213764 | 11/2018 |
| WO | 2018/218242 | 11/2018 |
| WO | WO 2019104115 | 5/2019 |
| WO | WO 2019126179 | 6/2019 |

OTHER PUBLICATIONS

International Search Report for PCT/US2018/033488, dated Aug. 8, 2018, 3 pages.
Written Opinion of the ISA for PCT/US2018/033488, dated Aug. 8, 2018, 5 pages.
International Preliminary Report on Patentability, dated Aug. 20, 2019, 25 pages.
Partial Supplementary European Search Report for Application No. 18802386.5 dated Mar. 10, 2021.
Sotgia, "Mitochondrial Markers Predict Recurrence, Metastasis and Tamoxifen-Resistance in Breast Cancer Patients: Early Detection of Treatment Failure with Companion Diagnostics", Oncotarget, 2017, vol. 8, No. 40, pp. 68730-68745.
Isidoro et al., "Breast Carcinomas Fulfill the Warburg Hypothesis and Provide Metabolic Markers of Cancer Prognosis", Carcinogenesis, vol. 26, No. 12, pp. 2095-2104, 2005. XP-002604220.
Giacometti et al., "In-vitro activity of macrolides alone and in combination with artemisin, atovaquone, dapsone, minocycline or pyrimethamine against *Cryptosporidium parvum*", Journal of Antimicrobial Chemotherapy, 1996, vol. 38, pp. 399-408.
M2 Pharma [London], "Study finds Vitamin C and antibiotics effectively killed cancer stem cells", Jun. 13, 2017, 2 pages.
Sotgia et al., "A mitochondrial based oncology platform for targeting cancer stem cells (CSCs): MITO-ONC-RX", Journal Cell Cycle, Sep. 26, 2018, vol. 17, No. 17, pp. 2091-2100.
Komatsu et al., "Clarithromycin enhances bortezomib-induced cytotoxicity via endoplasmic reticulum stress-mediated CHOP (GADD153) induction and autophagy in breast cancer cells", International Journal of Oncology, vol. 40, 2012, pp. 1029-1039.
Moriya et al., "Macrolide antibiotics block autophagy flux and sensitize to bortezomib via endoplasmic reticulum stress-mediated CHOP induction in myeloma cells", International Journal of Oncology, vol. 42, 2013, pp. 1541-1550.
Petovari et al., "Targeting cellular metabolism using rapamycin and/or doxycycline enhances anti-tumour effects in human glioma cells", Cancer Cell Int., 18:211, 2018, pp. 1-17.
Van Nuffel et al., "Repurposing Drugs in Oncology (ReDO)— clarithromycin as an anti-cancer agent", ecancermedicalscience, 2015, pp. 1-26.
Jankowitsch et al., "A novel N,N-8-amino-8-demethyl-D-riboflavin dimethyltransferase (RosA) catalyzing the two terminal steps of roseoflavin biosynthesis in *Streptomyces davawensis*", The American Society for Biochemistry and Molecular Biology, Inc., 2011, pp. 1-25.
Murphy, "Targeting lipophilic cations to mitochondria", Biochimica et Biophysica Acta, 2008, pp. 1028-1031.
Ross et al., "Lipophilic Triphenylphosphonium Cations as Tools in Mitochondrial Bioenergetics and Free Radical Biology", Biochemistry (Moscow), vol. 70, No. 2, 2005, pp. 222-230. [Translated from Biokhimiya].
Gonzalez et al., "Mitochondria, Energy and Cancer: The Relationship with Ascorbic Acid", JOM, vol. 25, No. 1, 2010, pp. 29-38.
Pubchem CID 240548. Mar. 26, 2005, pp. 1-19. Retrieved from the Internet https://pubchem.ncbi.nlm.nih.gov/compound/240548; p. 3 formula.
Pubchem CID 110135536, Jan. 18, 2016, pp. 1011. Retrieved from the Internet https://pubchem.ncbi.nlm.nih.gov/compound/110135536; p. 3, formula.
Ozsvari, B et al., 'Mitoriboscins: Mitochondrial-based therapeutics targeting cancer stem cells (CSCs), bacteria and pathogenic yeast'; Jul. 7, 2017, Oncotarget, vol. 8, No. 40, pp. 67457-67472: entire document.
Jerome Gilleron et al: "identification of siRNA delivery enhancers by a chemical library screen", Nucleic Acids Research, vol.43, No. 16, Jul. 28, 2015 (Jul. 28, 2015), pp. 7984-8001, XP055547439, ISSN: 0305-1048, DOI: 10.1093/nar/gkV762, abstract, p. 7984, right column, line 11, reference (4), p. 7994,1eft column, last line, reference (36), p. 7999, left column, reference 4, p. 8000, left column, reference 36.
Database CA [Online] Chemical Abstracts Service, Columbus, Ohio, US; Guo, Chun et al: "Synthesis and bioactivity of N, N'-Bis-substituted urea derivatives as novel small molecular inhibitors of cysteine protease of Trypanosoma cruzi", XP002788354, retrieved from STN Database accession No. 20042912828 * abstract * -& Guo, Chun et al: "Synthesis and bioactivity of N, N'-Bis-substituted urea derivatives as novel small molecular inhibitors of cysteine protease of Trypanosoma cruzi", Zhongguo Yaoke Daxue Xuebao, 34(6), 491-495 CODEN: ZHYXE9; ISSN: 1000-5048, 2003, XP009510743, table I, p. 495, abstract.
H. Ottosson et al: "Potent Inducers of Endogenous Antimicrobial Peptides for Host Directed Therapy of Infections". Scientific Reports, vol. 6, No. I, Nov. 9, 2016 (Nov. 9, 2016), XP055547477, DOI: 10.1038/sre236692 figure 1; cornpound 13, abstract.
Helen Ha et al: "Discovery of Novel CXCRZ Inhibitors Using Ligand-Based Pharmacophore Models", Journal of Chemical Information and Modeling, vol. 55, No. 8, Jul. 23, 2015 (Jul. 23, 2015), pp. 1720-1738, XP055547587, US, ISSN: 1549-9596, DOI: 10.1021/

(56) References Cited

OTHER PUBLICATIONS acs.jcim.5b00181, abstract. -& Helen Ha et al: "Supplementary materials and methods to: Discovery of Novel CXCRZ Inhibitors Using Ligand-Based Pharmacophore Models", Journal of Chemical Information and Modeling, vol. 55, No. 8, Aug. 24, 2015 (Aug. 24, 2015), pp. 1720-1138, XP055547978, US, ISSN: 1549-9596, DOI: 10.1021/acs.jcim.5b00181 Supplementary table 2, compound 24*.
Timmy Mani et al: "Probing Binding and Cellular Activity of Pyrrolidinone and Piperidinone Small Molecules Targeting the Urokinase Receptor", CHEMMEDCHEM, vol. 8. No. 12, Dec. 12, 2013 (Dec. 12, 2013), pp.s 1963-1977, XP55386919, DE, ISSN: 1860-7179, DOI: 10. 1002/cmdc.201300340, p. 1966, table 1; compound 1f, abstract *.
Ohta et al: "Novel 5-hydroxytryptamine (5-HT3) receptor antagonists. II. Synthesis and structure-activity relationships of 4,5,6,7-tetrahydro-1H-benzirnidazole derivatives", Chem Pharm. Bull, Jan. 1, 1996 (Jan. 1, 1996), pp. 1000-1008, XP055547596, Retrieved from the Internet: URL:https://www.jstage.jst.go.jp/article/c_pb1958/44/5/44_5_1000/_pdf/-char/en [retrieved on Jan. 25, 2019] p. 1002; table 2; compound 5e, abstract.
Database Registry [Online] Chemical Abstracts Service, Columbus, Ohio, US; Jan. 26, 2017 (Jan. 26, 2017), XP002788355, retrieved from STN, Database accession No. 2059764-23-5, abstract.
Database Registry [Online] Chemical Abstracts Service, Columbus. Ohio, US; Jan. 25, 2011 (Jan. 25, 2011). XP002788356, Database accession No. 2058655-99-3, abstract.
Database Registry [Online] Chemical Abstracts Service, Columbus, Ohio, US; Jan. 31, 2017 (Jan. 31, 2017), XP002788357, Database accession No. 2062025-32-3, abstract.
Bela Ozsvari et al: "Mitoriboscins: Mitochondrial-based therapeutics targeting cancer stem cells (CSCs), bacteria and pathogenic yeast", ONCOTARGET, vol. 8, No. 40, Sep. 15, 2017 (Sep. 15, 2017), p. 67457-67472, XP55546993, DOI: 10.18632/oncotarget.19084, the whole document.
Database Registry [Online] Chemical Abstracts Service, Columbus, Ohio US; Sep. 14, 2017 (Sep. 14, 2017). XP002788358, Database accession No. 2127176-25-2, abstract.
Database Registry [Online] Chemical Abstracts Service, Columbus, Ohio, US; Oct. 13, 2017 (Oct. 13, 2017), XP002788359, Database accession No. 2134616-41-2, abstract.
Database Registry [Online] Chemical Abstracts Service, Columbus, Ohio, US; Sep. 17, 2011 (Sep. 17, 2011), XP002788360, Database accession No. 2128079-22-9, abstract.
Database Recistry [Online] Chemical Abstracts Service, Columbus, Ohio, US; Sep. 14, 2017 (Sep. 14, 2017), XP002788361, Database accession No. 2127204-21-9, abstract.
MartinezOuschoorn U. E. et al. Cell Cycle of title "Ketone bodies and two-compartment tumor metabolism: stromal ketone production fuels mitochondrial biogenesis in epithelial cancer cells" published on Nov. 1, 2012.
CAS Registry 1047743-48-5 of Title "5-nitro-N-[2-(1-pyrrolidinyl)ethyl]-β-[3-(trifluoromethyl)phenyl]-1H-indol-3-propanamide"published on Sep. 9, 2008.
Cas Reg No. 1047387-08-5, STN Entry Date: Sep. 7, 2008; 1H-Indole-3-propanamide, 1-methyl-N-[2-(1-piperidinyl)ethyl]-β-[3-(trifluoromethyl)phenyl]-.
Cas Reg No. 1022389-70-3, STN Entry Date: May 25, 2008; 1H-Indole-3-propanamide, 1-methyl-β-(3- methylphenyl)-N-[2-(1-piperidinyl)ethyl]-.

* cited by examiner

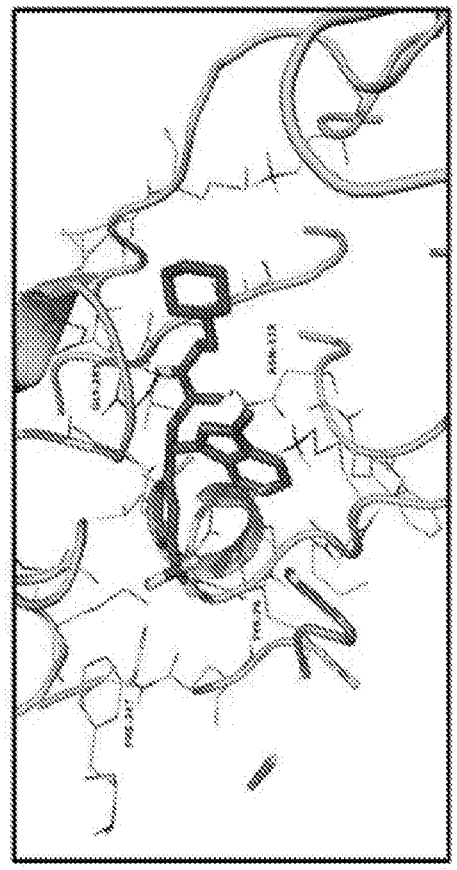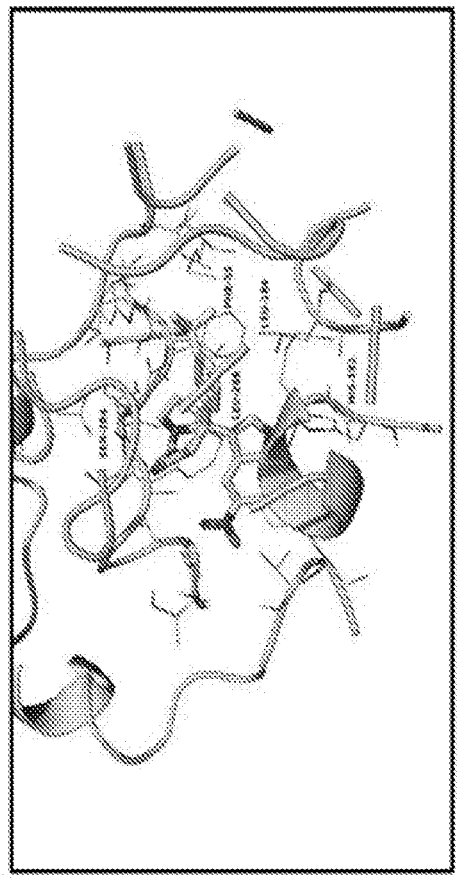
FIG. 6A
FIG. 6B

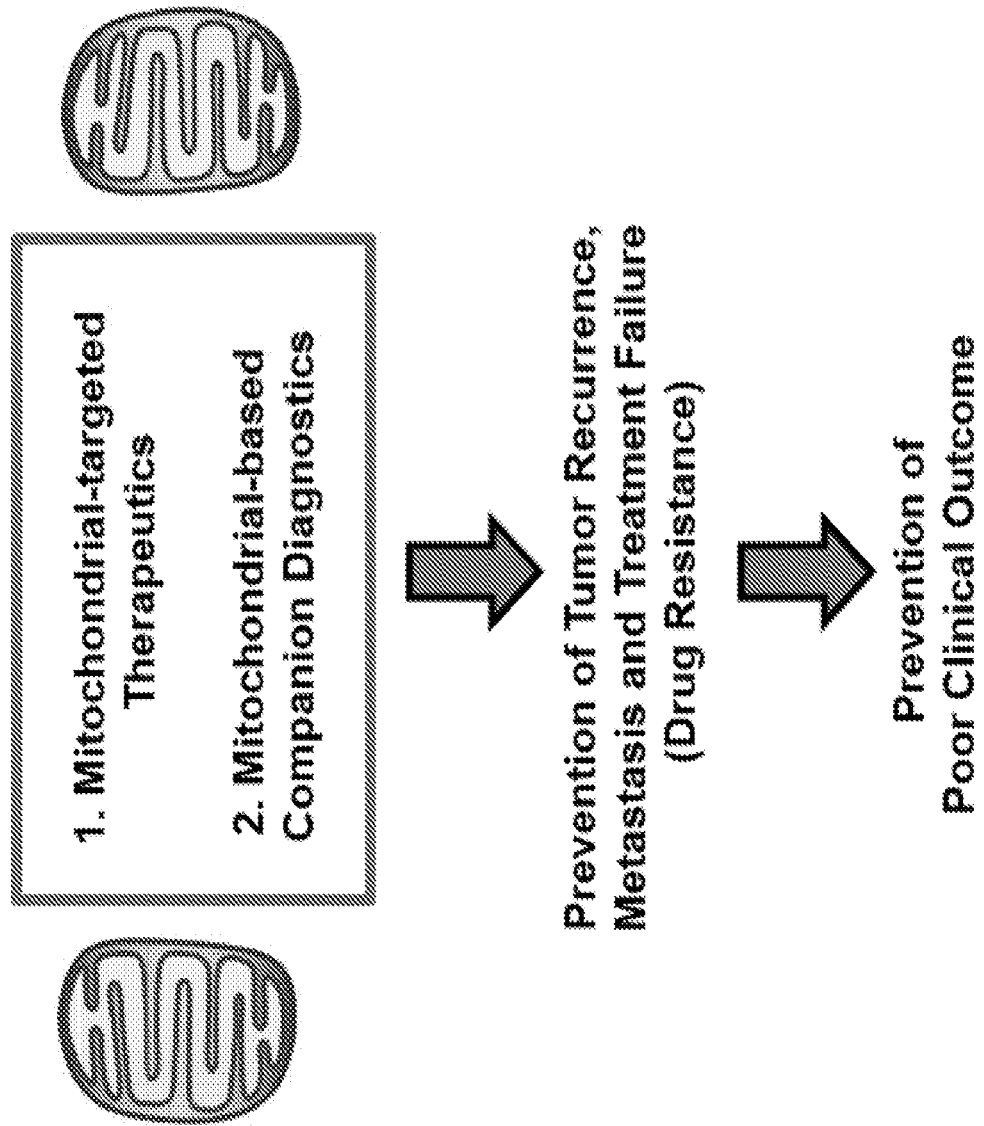

COMPANION DIAGNOSTICS FOR MITOCHONDRIAL INHIBITORS

CROSS REFERENCE TO RELATED APPLICATIONS

This application is the U.S. national phase of International Application No. PCT/US2018/033488 filed May 18, 2018, which designated the U.S. and claims the benefit of U.S. Provisional Application No. 62/508,799, filed May 19, 2017, U.S. Provisional Application No. 62/508,788, filed May 19, 2017, U.S. Provisional Application No. 62/508,769, filed May 19, 2017, U.S. Provisional Application No. 62/508,750, filed May 19, 2017, U.S. Provisional Application No. 62/529,871, filed Jul. 7, 2017, U.S. Provisional Application No. 62/524,829, filed Jun. 26, 2017, U.S. Provisional Application No. 62/576,287, filed Oct. 24, 2017, U.S. Provisional Application No. 62/590,432, filed Nov. 24, 2017, and Patent Cooperation Treaty Application No. PCT/US2018/022403, filed Mar. 14, 2018, the contents of which are incorporated by reference in their entireties. U.S. Provisional Application No. 62/471,688, filed Mar. 15, 2017, is also incorporated by reference in its entirety.

FIELD

The present disclosure relates to diagnostic kits and methods for identifying patients that may be responsive to mitochondrial inhibitor therapies to target and eradicate cancer stem cells.

BACKGROUND

Researchers have struggled to develop new anti-cancer treatments. Conventional cancer therapies (e.g. irradiation, alkylating agents such as cyclophosphamide, and anti-metabolites such as 5-Fluorouracil) have attempted to selectively detect and eradicate fast-growing cancer cells by interfering with cellular mechanisms involved in cell growth and DNA replication. Other cancer therapies have used immunotherapies that selectively bind mutant tumor antigens on fast-growing cancer cells (e.g., monoclonal antibodies). Unfortunately, tumors often recur following these therapies at the same or different site(s), indicating that not all cancer cells have been eradicated. Relapse may be due to insufficient chemotherapeutic dosage and/or emergence of cancer clones resistant to therapy. Hence, novel cancer treatment strategies are needed.

Advances in mutational analysis have allowed in-depth study of the genetic mutations that occur during cancer development. Despite having knowledge of the genomic landscape, modern oncology has had difficulty with identifying primary driver mutations across cancer subtypes. The harsh reality appears to be that each patient's tumor is unique, and a single tumor may contain multiple divergent clone cells. What is needed, then, is a new approach that emphasizes commonalities between different cancer types. Targeting the metabolic differences between tumor and normal cells holds promise as a novel cancer treatment strategy. An analysis of transcriptional profiling data from human breast cancer samples revealed more than 95 elevated mRNA transcripts associated with mitochondrial biogenesis and/or mitochondrial translation. Sotgia et al., *Cell Cycle*, 11(23):4390-4401 (2012). Additionally, more than 35 of the 95 upregulated mRNAs encode mitochondrial ribosomal proteins (MRPs). Proteomic analysis of human breast cancer stem cells likewise revealed the significant overexpression of several mitoribosomal proteins as well as other proteins associated with mitochondrial biogenesis. Lamb et al., *Oncotarget*, 5(22):11029-11037 (2014).

Functional inhibition of mitochondrial biogenesis using the off-target effects of certain bacteriostatic antibiotics or OXPHOS inhibitors provides additional evidence that functional mitochondria are required for the propagation of cancer stem cells. The inventors recently showed that a mitochondrial fluorescent dye (MitoTracker) could be effectively used to enrich and purify cancer stem-like cells (CSCs) from a heterogeneous population of living cells. Farnie et al., *Oncotarget*, 6:30272-30486 (2015). Cancer cells with the highest mitochondrial mass had the strongest functional ability to undergo anchorage-independent growth, a characteristic normally associated with metastatic potential. The 'Mito-high' cell sub-population also had the highest tumor-initiating activity in vivo, as shown using pre-clinical models. The inventors also demonstrated that several classes of non-toxic antibiotics could be used to halt CSC propagation. Lamb et al., *Oncotarget*, 6:4569-4584 (2015). Because of the conserved evolutionary similarities between aerobic bacteria and mitochondria, certain classes of antibiotics or compounds having antibiotic activity can inhibit mitochondrial protein translation as an off-target side-effect.

SUMMARY

In view of the foregoing background, it is an object of this disclosure to demonstrate methods for identifying a patient for anti-mitochondrial therapy. Methods may include obtaining a sample from the patient; determining the level of at least one mitochondrial marker in the sample; classifying the patient as a candidate for therapy with an anti-mitochondrial therapy if the sample is determined to have an increased level of the at least one mitochondrial marker relative to a threshold level. Methods include collecting samples from lung, breast, ovarian, gastric, skin, kidney, pancreas, rectum, colon, prostate, bladder, epithelial, and non-epithelial tissue sample. In some embodiments, the sample is a body fluid such as blood, serum, plasma, saliva, sputum, milk, tears, urine, ascites, cyst fluid, pleural fluid, and cerebral spinal fluid. In some embodiments, the sample includes circulating tumor cells isolated from at least one of serum, plasma, and blood.

The present disclosure includes using mitochondrial protein, RNA, and/or DNA as a mitochondrial marker. The mitochondrial marker may relate to or regulate beta-oxidation and/or ketone metabolism. Such markers include HSD17B10, BDH1, ACAT1, ACADVL, ACACA, ACLY, HADHB, SUCLG2, ACAD9, HADHA, ECHS1, and ACADSB.

In some embodiments, the mitochondrial marker relates to or regulates at least one of mitochondrial biogenesis, electron transport, metabolism, ATP synthesis, ADP/ATP exchange/transport, CoQ synthesis, ROS production, and suppression of glycolysis, autophagy and/or mitophagy. Such markers include HSPA9, TIMM8A, GFM1, MRPL45, MRPL17, HSPD1(HSP60), TSFM, TUFM, NDUFB10, COX6B1, PMPCA, COX5B, SDHA, UQCRC1, CHCHD2, ATP5B, ATPIF1, ATP5A1, ATP5F1, ATP5H, ATP5O, SLC25A5, COQ9, GPD2, SOGA1, and LRPPRC. In some embodiments, the mitochondrial marker regulates at least one enzymes ACAT1/2 and/or OXCT1/2.

The present disclosure further relates to methods of administering to the patient having an increased level of at least one mitochondrial marker at least mitochondrial inhibitor. The mitochondrial inhibitor may be a mitoriboscin, a mitoketoscin, a antimitoscin, metformin, a tetracycline family member, a erythromycin family member, atovaquone, bedaquiline, vitamin c, caffeic acid phenyl ester, and berberine. In some embodiments, the tetracycline family member is doxycycline. In some embodiments, the erythromycin family member is azithromycin.

The present disclosure also relates to methods of administering to the patient an anti-angiogenic agent. Anti-angiogenic agents include angiostatin, bevacizumab, arresten, canstatin, combretastatin, endostatin, NM-3, thrombospondin, tumstatin, 2-methoxyestradiol, Vitaxin, Getfitinib, ZD6474, erlotinib, CI1033, PKI1666, cetuximab, PTK787, SU6668, SU1 1248, trastuzumab, Marimastat, COL-3, Neovastat, 2-ME, SU6668, anti-VEGF antibody, Medi-522 (Vitaxin E), tumstatin, arrestin, recombinant EPO, troponin I, EMD121974, IFN-α celecoxib, PD0332991, tamoxifen, paclitaxel (taxol) and thalidomide. In some embodiments, the anti-angiogenic agent is administered simultaneously or sequentially with a mitochondrial inhibitor.

The present disclosure also relates to diagnostic kits for measuring one or more mitochondrial markers (companion diagnostics) to identify a high-risk cancer patient population that is most likely to benefit from anti-mitochondrial therapy. In some embodiments, the kit may include a component for measuring for measuring levels of mitochondrial marker RNA, DNA, and/or protein relative to a normal control. In some embodiments, the mitochondrial marker is measured by any number of ways known in the art for measuring RNA, DNA, and or protein, including quantitative PCR and/or RT-PCR kits, microarrays, Northern blots, and Western blots. In some embodiments, the kit may include an antibody specific to a mitochondrial marker. The antibody may be a monoclonal or a polyclonal antibody. In some embodiments, the kit may include a molecule that binds to at least one of a mitochondrial ribosomal protein (MRP), an OXPHOS complex, and a mitochondrial membrane protein/chaperone.

BRIEF DESCRIPTION OF THE DRAWINGS

FIG. 6A shows a docking image of Compound 2 docking at a succinyl-CoA binding site of 3-oxoacid CoA-transferase 1 (OXCT1). FIG. 6B shows a docking image of Compound 8 docking at a CoA binding site of human acetyl-CoA acetyltransferase (ACAT1).

FIG. 12 shows the basic components of a mitochondrial-based oncology platform.

DESCRIPTION

Figure 1B:
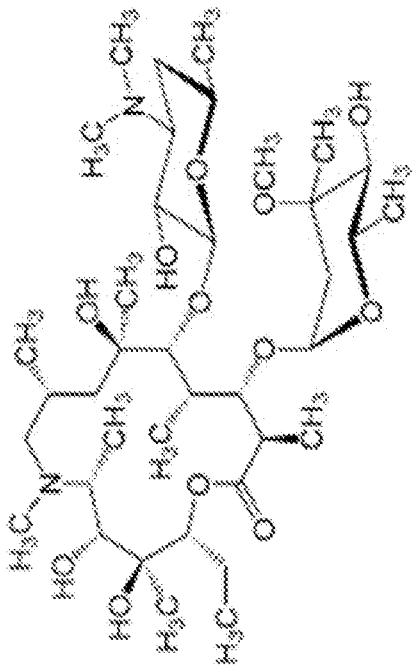
FIGS. 1A-E illustrate the structures of antibiotics that may be used inhibit the propagation of cancer stem cells (CSCs).
Figure 1D:
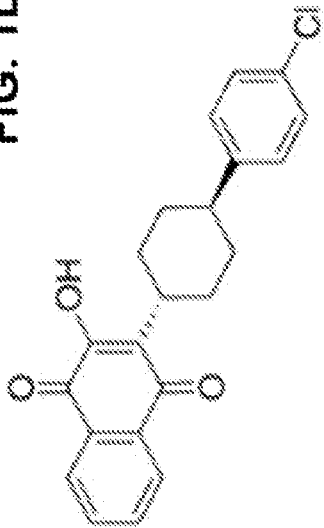
Figure 1A:
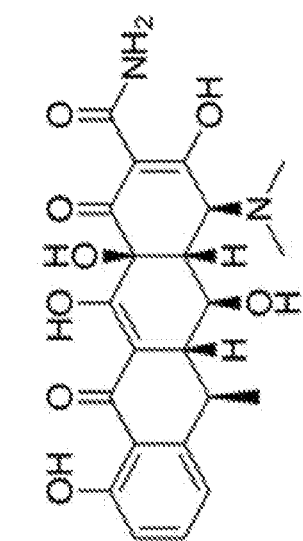
Figure 1C:
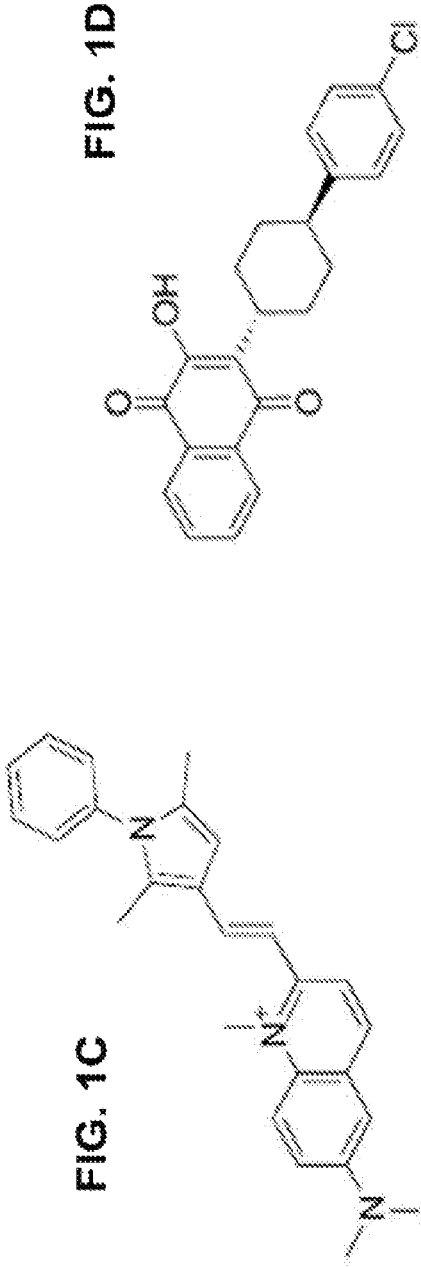
Figure 1E:
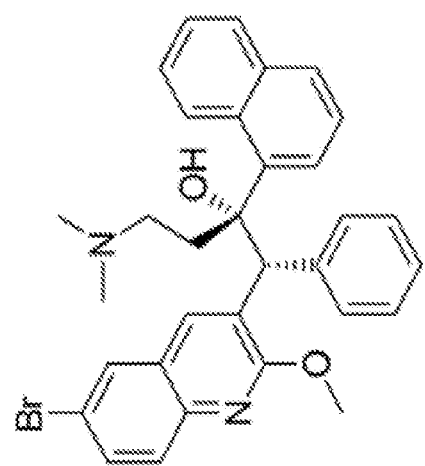
Figure 2A:
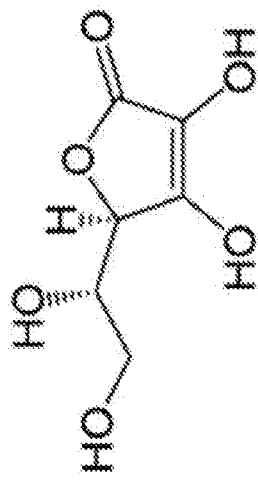
FIGS. 2A-D illustrate the structures of naturally occurring compounds that may be used to inhibit the propagation of CSCs.
Figure 2B:
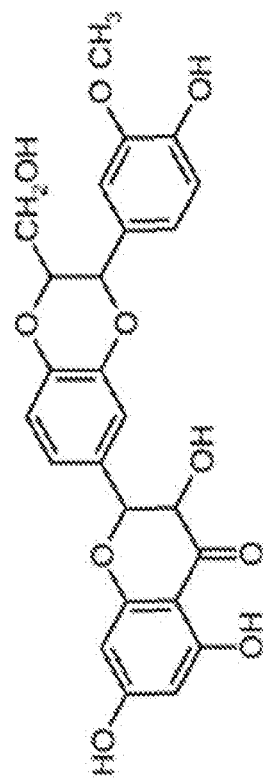
Figure 2C:
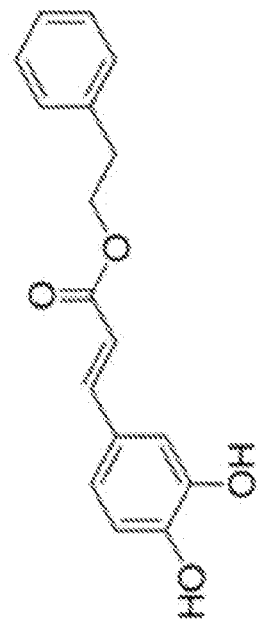
Figure 2D:
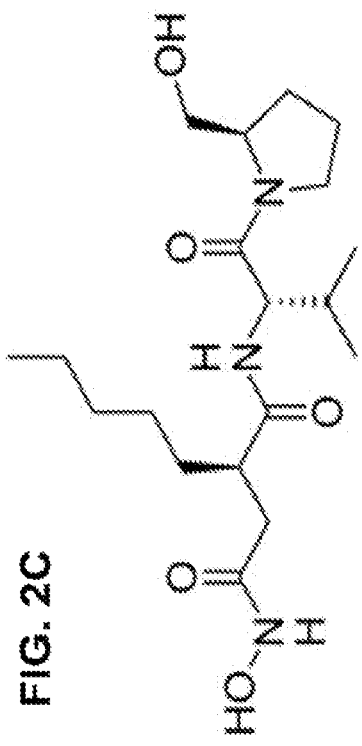
Figure 3B:
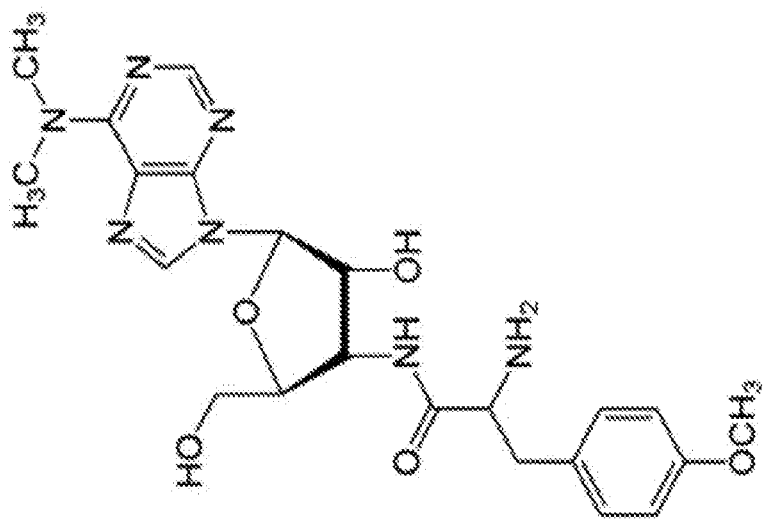
FIGS. 3A-C illustrate the structures of experimental compounds that may be used to inhibit the propagation of CSCs.
Figure 3A:
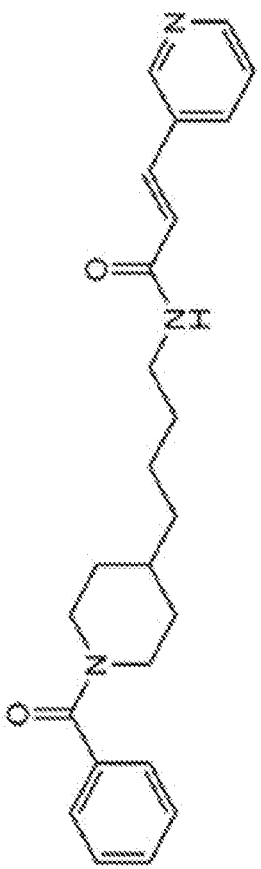
Figure 3C:
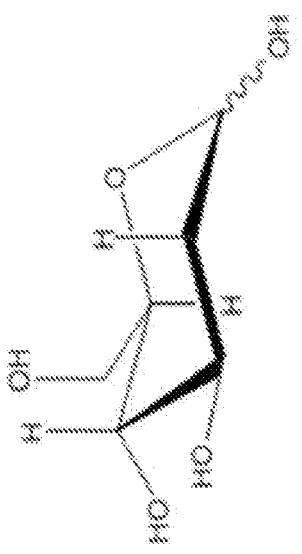
Figure 4B:
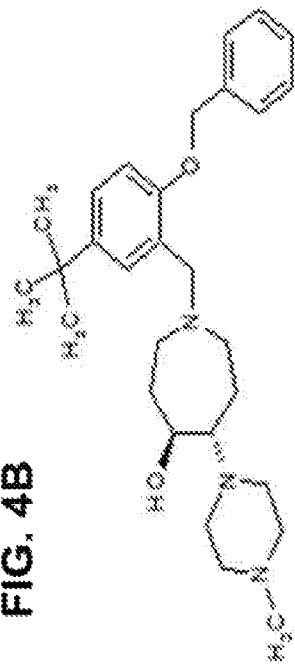
FIGS. 4A-D illustrate the structure of exemplary mitoriboscins.
Figure 4A:
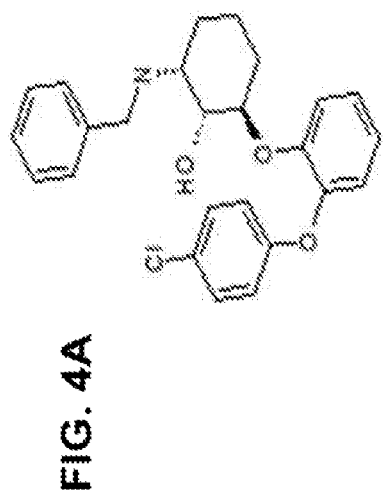
Figure 4D:
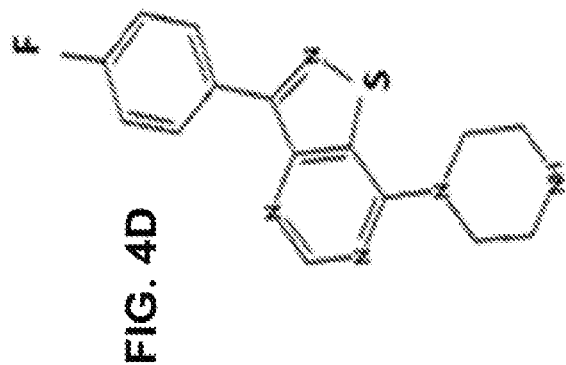
Figure 4C:
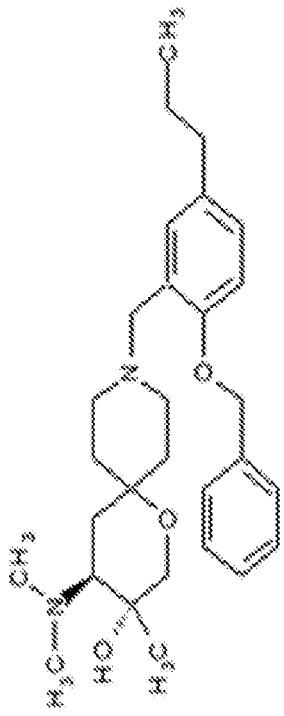

The following description illustrates embodiments of the present approach in sufficient detail to enable practice of the present approach. Although the present approach is described with reference to these specific embodiments, it should be appreciated that the present approach can be embodied in different forms, and this description should not be construed as limiting any appended claims to the specific embodiments set forth herein. Rather, these embodiments are provided so that this disclosure will be thorough and complete, and will fully convey the scope of the present approach to those skilled in the art.

Tumors and their microenvironment are heterogeneous structures that behave like metabolic ecosystems. It is well accepted that more than a single type of cancer cell exists. For example, within a given epithelial cancer cell line (such as MCF7 cells), there are "bulk" cancer cells (~85-95%; the majority of the population), as well as various types of progenitor cells (less than 5%), and cancer stem cells (CSCs; less than 1%). CSCs and progenitor cells are thought to be the most dangerous as they behave as tumor-initiating cells (TICs) in vivo and can undergo metastasis. In contrast, "bulk" cancer cells are largely non-tumorigenic.

Because CSCs are relatively "rare", little is known about their metabolic properties. The inventors previously showed that cells may be functionally enriched for CSCs by trypsinizing the entire cell population and seeding it as a single-cell suspension onto low-attachment plates. Under such conditions, the majority (more than 90%) of "bulk" cancer cells die via apoptosis, while only the CSCs survive and propagate, ultimately resulting in the formation of 3D spheroid structures after about 5 days. Each 3D spheroid is clonally formed from a single CSC. For breast CSCs, these 3D spheroids are also known as tumor-spheres or mammospheres. The generation of these 3D spheroids is thought to mimic the process of tumor formation and/or metastasis, thus providing a model for drug discovery and functional validation.

To understand the metabolic differences between "bulk" cancer cells and CSCs, the inventors previously compared cultured breast cancer cells grown either as monolayers or 3D spheroids. These cells were subjected to profiling via unbiased label-free proteomics analysis. The inventors found that over 60 nuclear-encoded mitochondrial proteins were specifically up-regulated in 3D spheroid structures relative to monolayer cells processed in parallel. Virtually identical results were obtained with two distinct ER(+) breast cancer cell lines (MCF7 and T47D; more than 40 overlapping mitochondrial proteins). Informatics analysis of the list of up-regulated mitochondrial proteins was consistent with an increase in mitochondrial mass, due either to i) increased mitochondrial biogenesis or ii) a shut down in mitophagy, or both. These results indicate that high mitochondrial mass is a characteristic feature of the CSC phenotype. These results also suggest that CSCs are dependent on OXPHOS and/or new mitochondrial biogenesis (protein translation) for survival and propagation. While testing this hypothesis, inventors showed that 3D spheroid formation is effectively blocked using specific mitochondrial inhibitors, such as oligomycin, which targets mitochondrial Complex V and shuts off ATP synthesis. However, oligomycin is toxic and cannot be used as an anti-cancer therapeutic. Thus, these results highlight the need for compounds that can target mitochondria in CSCs without inducing deleterious side effects in normal cells.

To further validate the functional relationship between high mitochondrial mass and "stemness", inventors employed staining with MitoTracker to metabolically fractionate an MCF7 cell line into "Mito-high" and "Mito-low" cell sub-populations. MitoTracker is a non-toxic fluorescent probe that can be used to directly measure mitochondrial mass in live cells by flow cytometry. As predicted, the "Mito-high" cell population, with increased mitochondrial mass, showed the greatest capacity for i) 3D spheroid formation and ii) tumor initiation in a pre-clinical animal model in vivo. Therefore, mitochondrial mass may be a critical determinant of stemness in cancer cells. Similarly, elevated telomerase activity (hTERT), a functional marker of proliferation and immortality in CSCs, was also specifically associated with high mitochondrial mass. The inventors hypothesized that a targeted reduction in mitochondrial mass or OXPHOS may be used to eradicate CSCs.

The inventors have recently focused efforts on the identification and repurposing of FDA-approved drugs that may be used to inhibit the propagation of CSCs. These antibiotics include members of the tetracycline family (doxycycline/ tigecycline), the erythromycin family (azithromycin), anti-parasitic drugs (pyrvinium pamoate and atovaquone), and antimicrobials targeting drug-resistant mycobacterium (bedaquiline; TB, tuberculosis). FIG. 1 provides exemplary structures of these antibiotics (FIGS. 1A-E show the structures of doxycycline, azithromycin, pyrvinium (pamoate salt; not shown), atovaquone, and bedaquiline, respectively). Table 1 lists exemplary antibiotics and shows which mitochondrial structure or process is targeted. For example, doxycycline and azithromycin inhibit mitochondrial protein translation, thereby inhibiting mitochondrial biogenesis as an off-target side effect. Pyrvinium pamoate and atovaquone inhibit OXPHOS (related to mitochondrial complex II/III) as a side effect. Bedaquiline inhibits ATP-synthase (mitochondrial complex V). Each of these antibiotics has been shown to inhibit anchorage-independent propagation of CSCs by targeting mitochondrial function.

TABLE 1

Exemplary FDA-approved drugs that may be used to eradicate CSCs.

| Drug Name | Inhibition of | FDA-approved |
| --- | --- | --- |
| Doxycycline | Mito Biogenesis | Yes |
| Tigecycline | Mito Biogenesis | Yes |
| Azithromycin | Mito Biogenesis | Yes |
| Pyrvinium pamoate | OXPHOS/Complex II | Yes |
| Atovaquone | OXPHOS/Complex III | Yes |
| Bedaquiline | Complex V | Yes |
| Palbociclib | CDK4/6 | Yes |

Inventors have also previously identified experimental and natural compounds that target CSCs, including glycolysis inhibitors (Vitamin C and Silibinin), mitochondrial inhibitors (Actinonin; CAPE, from Honey bee propolis), and inhibitors of protein synthesis (puromycin) and NAD(+) recycling (FK-866). As CSCs appear to be highly proliferative, due to their over-expression of telomerase (hTERT), they are sensitive to Palbociclib, an FDA-approved CDK4/6 inhibitor, with an IC-50 of ~100 nM. Therefore, inhibition of CSC proliferation is an alternative or could be used in conjunction with other cancer therapies.

Doxycycline shows many other anti-cancer properties that may be further explored. For example, Doxycycline behaves as a radio-sensitizer, making CSCs approximately 3 to 5 times more sensitive to radiation treatment. In addition, Doxycycline effectively targets hypoxic CSCs and overcomes Paclitaxel-resistance under conditions of hypoxia; this may have important implications for achieving more effective anti-angiogenic therapy. Doxycycline appears to be effective as a mutation-independent approach for targeting CSCs as it inhibits both activated H-Ras (G12V) and c-Myc oncogenes as well as other environmental oncogenic stimuli (mitochondrial oxidative stress/ROS), via the specific targeting of mitochondrial biogenesis.

One concern with doxycycline therapy is the potential for the development of drug-resistance in CSCs. To investigate this issue, the inventors developed and characterized the phenotypic behavior of Doxy-resistant (DoxyR)-MCF7 cells. The inventors found that DoxyR-CSCs show a significant shift towards aerobic glycolysis due to a loss of mitochondrial function, which ultimately results in metabolic inflexibility. (DoxyR)-MCF7 cells showed an up to 35-fold loss of mitochondrial-DNA encoded proteins (mt-DNA) that are required for OXPHOS activity, such as MT-ND3, MT-CO2, MT-ATP6 and MT-ATP8. DoxyR-CSCs appeared to be more "quiescent", with greater than 50% reductions in proliferation and cell migration, as well as a significantly impaired ability to form 3D spheroids. The inventors showed that DoxyR-CSCs are sensitive to other metabolic therapies, including inhibitors of i) OXPHOS (Atovaquone, Irinotecan, Sorafenib, Niclosamide), ii) glycolysis (Vitamin C and Stiripentol) and iii) autophagy (Chloroquine). A listing of these drugs and their targets is provided in Table 2. Therefore, the efficacy of doxycycline treatment may be improved by developing combination therapies with other metabolic inhibitors, based on the concepts of metabolic inflexibility and synthetic lethality in cancer cells.

TABLE 2

Exemplary drugs used in conjugation with doxycycline to eradicate CSCs.

| Drug Name | Target | FDA-approved |
| --- | --- | --- |
| Atovaquone | OXPHOS | Yes |
| Irinotecan | OXPHOS | Yes |
| Sorafenib | OXPHOS | Yes |
| Niclosamide | OXPHOS | Yes |
| Berberine | OXPHOS | Natural supplement |
| 2-deoxy-glucose (2-DG) | Glycolysis | Experimental |
| Vitamin C | Glycolysis | Natural supplement |
| Stiripentol | Glycolysis | Clinically-approved (EU/CA/JP) |
| Chloroquine | Autophagy | Yes |

The inventors have also focused efforts on the development of therapeutics that focus on specific mitochondrial targets. Exemplary therapeutics are listed in Table 3.

TABLE 3

Exemplary therapeutics that focus on mitochondrial targets.

| Drug Name | Target | Metabolic Process/Mechanism |
|---|---|---|
| Mitoriboscins | Mitochondrial Ribosome | Mitochondrial Protein Synthesis |
| Mitoketoscins | OXCT1/ACAT1 | Mitochondrial Ketone Metabolism |
| Mitoflavoscins | Mito Complex VII | Flavin-containing proteins (Vit-B2) |
| Tri-phenyl-phosphonium (TPP) | Mitochondria | Mitochondrial-targeting-signal (MTS) |

One family of therapeutics, coined "mitoriboscins," are mito-ribosome inhibitors that inhibit mitochondrial protein synthesis. FIG. 4A-D illustrates examples of mitoriboscins. The inventors identified these compounds by combining computational chemistry (in silico drug design in which the target used was the 3D structure of the large mitochondrial ribosome, as determined by cryo-electron microscopy) with phenotypic library screening to detect ATP depletion.

Figure 5:
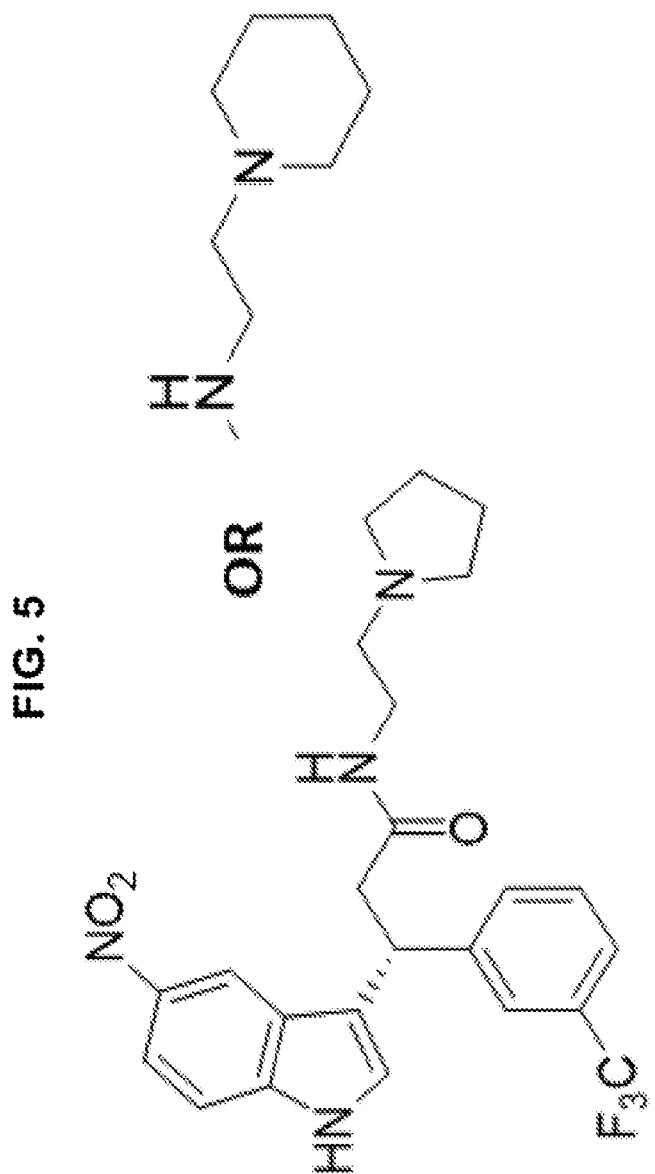
FIG. 5 illustrates an exemplary pharmacophore for a mitoketoscin.

By targeting the mitochondrial enzymes OXCT1 and ACAT1, inventors also developed mitochondrial inhibitors that interfere with ketone metabolism (these compounds mimic the structure of CoA). These compounds are known as "mitoketoscins." FIG. 5 illustrates a pharmacophore for a mitoketoscin. FIG. 6A illustrates the docking of Compound 2 (a hit for an OXCT1 screen) at the succinyl-CoA binding site of OXCT1. FIG. 6B illustrates the docking of Compound 8 (a hit for an ACAT1 screen) at the CoA binding site of human ACAT1.

Figure 7:
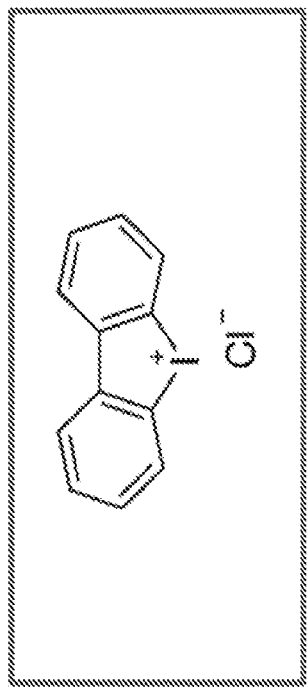
FIG. 7 shows the structures of diphenyleneiodium chloride (DPI) and 2-butene-1,4-bis-triphenylphosphonium (TPP).
Figure 7:
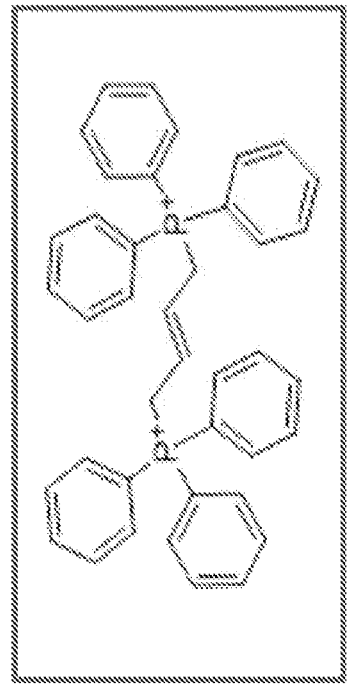

Inventors also identified compounds named "mitoflavoscins," compounds that bind to flavin-containing enzymes and inhibit mitochondrial function. Such compounds may be designed to target and deplete FMN, FAD, and/or riboflavin. The inventors identified an approach to acutely induce a Vitamin B2 (riboflavin) deficiency that potently inhibits CSC propagation, with an IC-50 of ~3 nM. This drug is approximately 30 times more potent than Palbociclib for targeting CSCs. FIG. 7 illustrates the structure of DPI, one embodiment of a mitoflavoscin.

Inventors also identified the use of tri-phenyl-phosphonium (TPP) to eradicate CSCs. TPP behaves as a mitochondrial targeting signal. FIG. 7 illustrates the structure of TPP. TPP compounds appear to be able to metabolically distinguish between "normal cell" mitochondria and "malignant" mitochondria of bulk cancer cells and CSCs, as the TPP compounds are non-toxic in normal human fibroblasts and yet block CSC propagation.

Figure 8A:
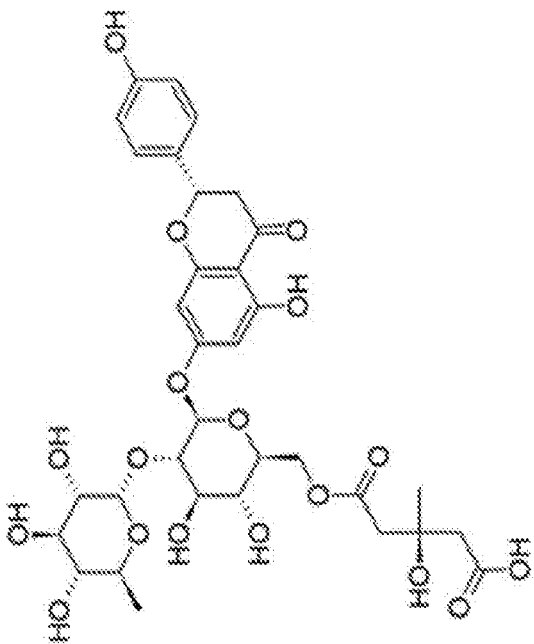
FIGS. 8A-C show the structures of brutieridin, melitidin, and mDIVI1, respectively.
Figure 8B:
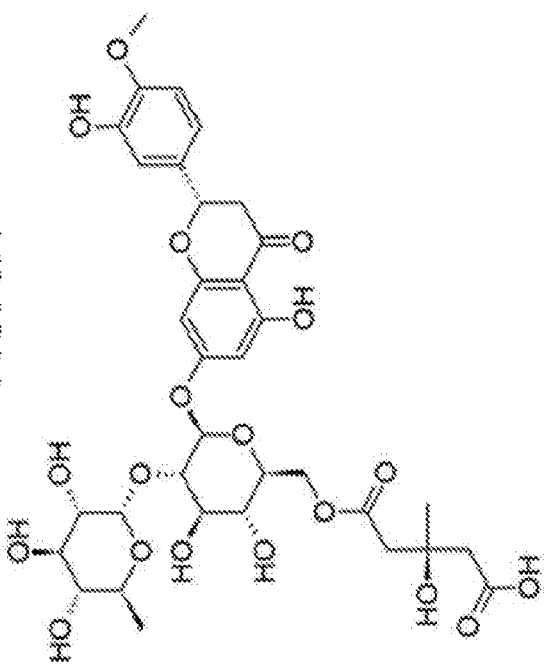
Figure 8C:
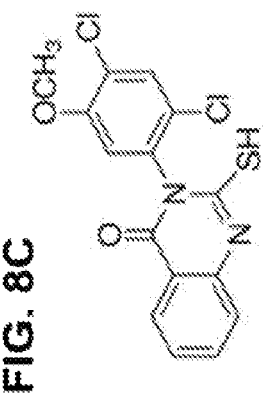

Inventors also investigated naturally-occurring mitochondrial inhibitors that may be used to more effectively target CSCs. A list of exemplary naturally-occurring mitochondrial inhibitors is provided in Table 4. The inventors found that brutieridin and melitidin, two compounds found in bergamot, act as statin-like drugs and inhibit mevolonate metabolism as well as CSC propagation. FIGS. 8A-B illustrate the structures of brutieridin and melitidin, respectively. FIG. 8C illustrates the structure of mDIVI1 for comparison. Interference with the normal process of mitochondrial fission-fusion cycles, such as by targeting the DRP1 protein, may represent a viable strategy for eradicating CSCs.

TABLE 4

Naturally-occurring mitochondrial inhibitors that target CSCs.

| Drug Name | Target | Metabolic Process Inhibited |
|---|---|---|
| mDIVI1 | DRP1* | Mitochondrial Fission/Fusion |
| Brutieridin | HMGR** | Mevalonate Metabolism |
| Melitidin | HMGR** | Mevalonate Metabolism |

*Dynamin-related protein 1
**3-hydroxy-3-methylglutaryl-CoA-reductase.

The identification and design of new mitochondrial inhibitors may have other medical applications and benefits such as the development of new anti-bacterial and anti-fungal agents and combating antibiotic-resistance. According to the ndo-symbiotic Theory of Mitochondrial Evolution", mitochondria first originated historically from the engulfment of aerobic bacteria, an event that occurred ~1.45 billion years ago. As a result, mitochondria share strong structural and functional similarities with bacteria, explaining the off-target effects of antibiotics, which often show manageable mitochondrial side-effects. Conversely, it would be predicted that mitochondrial inhibitors may also show some moderate anti-bacterial and anti-fungal side effects.

To directly test this hypothesis, the inventors evaluated the anti-bacterial and anti-fungal activity of exemplary mitoriboscins. Several mitoriboscins showed anti-bacterial activity towards both gram-positive and gram-negative organism(s), pathogenic yeast (Candida albicans) and Methicillin-resistant Staphylococcus aureus (MRSA). Therefore, using cancer cells for initial drug screening may also be useful for developing new antibiotics to combat drug-resistant micro-organisms.

Figure 10A:
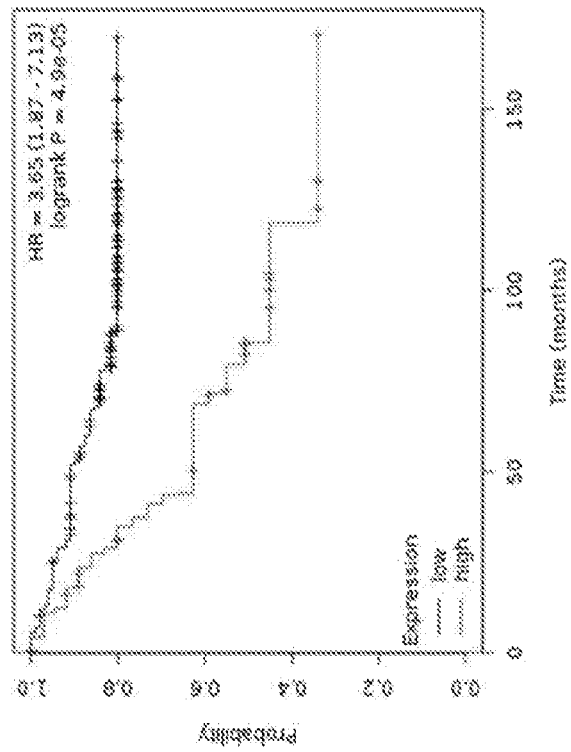
FIGS. 10A-B show the probability of recurrence and distant metastasis, respectively, of patients having specific Mito-Signatures.
Figure 10B:
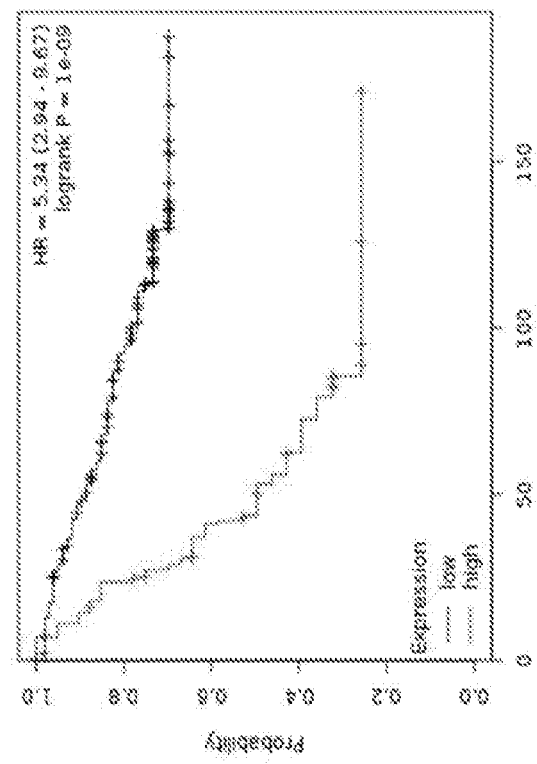
Figure 11B:
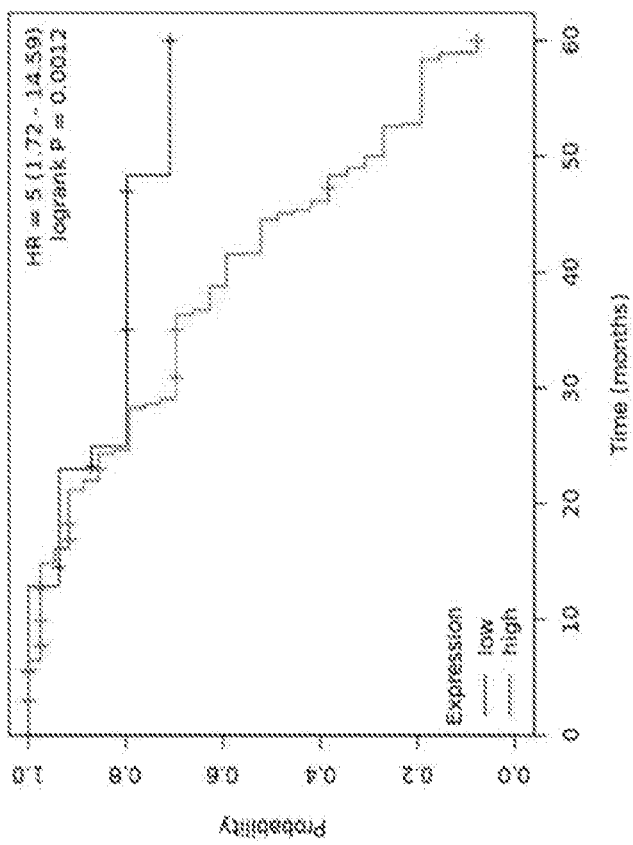
FIGS. 11A-B show the probability of overall survival in patients having a specific Mito-Signature and undergoing platin or taxol treatment, respectively.
Figure 11A:
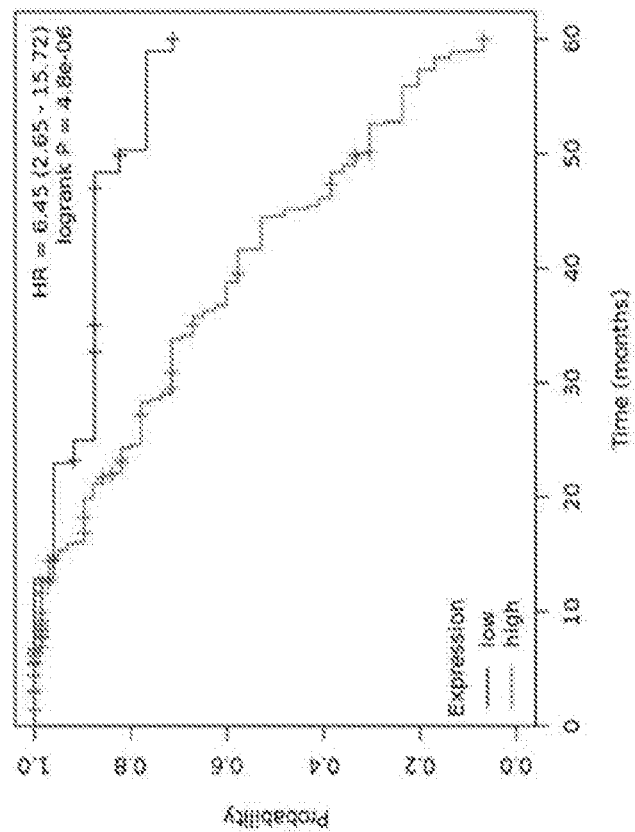

Over one thousand mitochondrial proteins are encoded by the nuclear genome. The inventors have begun to assess their potential prognostic value as biomarkers and companion diagnostics. The inventors hypothesize that the over-expression of a given mitochondrial protein in cancer cells and CSCs may be associated with tumor recurrence and metastasis, due to the emergence of drug resistance, and ultimately resulting in treatment failure. To test this hypothesis, the inventors used an online survival-analysis tool to perform Kaplan-Meier (K-M) studies on more than 400 nuclear mitochondrial gene transcripts to interrogate publicly available microarray data from patients with four distinct epithelial cancer types: i) breast, ii) ovarian, iii) lung and iv) gastric. In all four anatomic cancer types, the inventors observed that the over-expression of mitochondrial gene transcripts is associated with poor clinical outcome. For example, this approach effectively predicted tamoxifen-resistance in ER(+) breast cancer patients (represented as recurrence and distant metastasis in FIGS. 10A-B, respectively), as well as Taxol and Platin resistance in ovarian cancer patients (represented as overall survival in FIGS. 11A-B, respectively). These results are functionally supported by further experimental observations demonstrating that Tamoxifen-resistant MCF7 cells (TAMR) show a significant increase in mitochondrial oxygen consumption and ATP production.

The present disclosure therefore relates to methods of predicting the sensitivity of neoplastic cell growth to anti-mitochondrial agents. The methods may include obtaining a sample of a neoplasm from a patient, determining the level of mitochondrial markers in the sample and comparing the level of mitochondrial markers to a control, and predicting the sensitivity of the neoplastic cell growth to inhibition by an anti-mitochondrial agent based on relative marker levels.

High expression levels of mitochondrial markers correlate with high sensitivity to inhibition by an anti-mitochondrial agent. Mitochondrial markers may be obtained from tumor biopsy samples and/or by isolating circulating tumor cells from serum, plasma, and/or blood samples. Mitochondrial markers may include mitochondrial RNAs, proteins, and/or mitochondrial DNA. In some embodiments, mitochondrial DNA may be obtained from body fluids (e.g., blood, serum, plasma, saliva, sputum, milk, tears, urine, ascites, cyst fluid, pleural fluid, and/or cerebral spinal fluid). Mitochondrial marker levels may be measured by any number of ways known in the art, including quantitative PCR and/or RT-PCR, microarrays, Northern blots, Western blots, etc.

In some embodiments, mitochondrial markers may include mitochondrial proteins, RNA, and/or DNA that are associated with or regulate beta-oxidation and/or ketone metabolism, such as HSD17B10, BDH1, ACAT1, ACADVL, ACACA, ACLY, HADHB, SUCLG2, ACAD9, HADHA, ECHS1, ACADSB. In some embodiments, mitochondrial markers may include mitochondrial proteins, RNA, and/or DNA that are involved in: mitochondrial biogenesis, such as HSPA9, TIMM8A, GFM1, MRPL45, MRPL17, HSPD1(HSP60), TSFM, TUFM; electron transport, such as NDUFB10, COX6B1, PMPCA, COX5B, SDHA, UQCRC1; metabolism, such as CHCHD2, ATP synthesis, such as ATP5B, ATPIF1, ATP5A1, ATP5F1, ATP5H, ATP5O; ADP/ATP exchange/transport, such as SLC25A5; CoQ synthesis, such as COQ9; ROS production, such as GPD2; and/or suppression of glycolysis, autophagy and mitophagy, such as SOGA1 and LRPPRC. In some embodiments, the mitochondrial markers may include mitochondrial proteins, RNA, and/or DNA related to the enzymes ACAT1/2 and/or OXCT1/2.

In some embodiments, the mitochondrial markers may include mitochondrial proteins, RNA, and/or DNA that are upregulated or increased in certain cancer types. For example, Table 5, adapted from U.S. Provisional Application No. 62/508,799, the contents of which is incorporated by reference in its entirety, shows exemplary proteins that may be used as mitochondrial biomarkers in gastric cancers. As is shown in Table 5, mitochondrial biomarkers may include mitochondrial proteins, RNA, and/or DNA associated with heat shock proteins and chaperones, membrane proteins, mitochondrial antioxidants, mitochondrial genome maintenance, large and/or small ribosomal subunits, and OXPHOS complexes. In some embodiments, two or more mitochondrial biomarkers may be used to create a "Mito-Signature", a predictor for clinical outcomes. An exemplary Mito-Signature for gastric cancer is shown in Table 6.

TABLE 5

Prognostic value of mitochondrial markers in gastric cancers.

| Gene Probe ID | Symbol | Hazard-Ratio | Log-Rank Test |
|---|---|---|---|
| Heat Shock Proteins and Chaperones (4 probes) | | | |
| 200807_s_at | HSPD1 | 1.83 | 1.9e−06 |
| 200806_s_at | HSPD1 | 1.56 | 0.003 |
| 200691_s_at | HSPA9 | 1.61 | 0.0002 |
| 205565_s_at | FXN | 1.38 | 0.01 |
| Membrane Proteins (9 probes) | | | |
| 208844_at | VDAC3 | 2.22 | 1.4e−09 |
| 211662_s_at | VDAC2 | 1.51 | 0.002 |
| 200955_at | IMMT | 2.20 | 2.4e−09 |
| 218118_s_at | TIMM23 | 1.91 | 4.2e−07 |
| 218408_at | TIMM10 | 1.88 | 1.4e−06 |

TABLE 5-continued

Prognostic value of mitochondrial markers in gastric cancers.

| Gene Probe ID | Symbol | Hazard-Ratio | Log-Rank Test |
|---|---|---|---|
| 218357_s_at | TIMM8B | 1.49 | 0.002 |
| 201821_s_at | TIMM17A | 1.33 | 0.025 |
| 201870_at | TOMM34 | 1.95 | 5.1e−07 |
| 202264_s_at | TOMM40 | 1.44 | 0.009 |
| Mitochondrial Anti-Oxidants (2 probes) | | | |
| 215223_s_at | SOD2 | 1.72 | 2.1e−05 |
| 215078_at | SOD2 | 1.70 | 2.9e−05 |
| Mitochondrial Genome Maintenance (3 probes) | | | |
| 208694_at | PRKDC | 2.05 | 1.2e−07 |
| 210543_s_at | PRKDC | 1.78 | 6.9e−06 |
| 215757_at | PRKDC | 1.47 | 0.003 |
| Large Ribosomal Subunit (12 probes) | | | |
| 204599_s_at | MRPL28 | 2.17 | 1.2e−08 |
| 221997_s_at | MRPL52 | 2.12 | 3.2e−09 |
| 222216_s_at | MRPL17 | 1.68 | 0.0001 |
| 220527_at | MRPL20 | 1.67 | 0.0002 |
| 217907_at | MRPL18 | 1.62 | 0.0004 |
| 218887_at | MRPL2 | 1.60 | 0.0002 |
| 203931_s_at | MRPL12 | 1.56 | 0.001 |
| 208787_at | MRPL3 | 1.53 | 0.0007 |
| 217919_s_at | MRPL42 | 1.52 | 0.002 |
| 218049_s_at | MRPL13 | 1.47 | 0.008 |
| 218281_at | MRPL48 | 1.40 | 0.009 |
| 213897_s_at | MRPL23 | 1.29 | 0.049 |
| Small Ribosomal Subunit (8 probes) | | | |
| 215919_s_at | MRPS11 | 1.89 | 5.1e−07 |
| 213840_s_at | MRPS12 | 1.84 | 1.5e−06 |
| 210008_s_at | MRPS12 | 1.47 | 0.004 |
| 204330_s_at | MRPS12 | 1.37 | 0.015 |
| 204331_s_at | MRPS12 | 1.37 | 0.037 |
| 203800_s_at | MRPS14 | 1.53 | 0.002 |
| 219220_x_at | MRPS22 | 1.44 | 0.005 |
| 219819_s_at | MRPS28 | 1.42 | 0.01 |
| 218112_at | MRPS34 | 1.36 | 0.02 |
| Complex I (11 probes) | | | |
| 201757_at | NDUFS5 | 2.27 | 6e−10 |
| 215850_s_at | NDUFA5 | 1.93 | 2.1e−07 |
| 208969_at | NDUFA9 | 1.92 | 1.5e−06 |
| 203606_at | NDUFS6 | 1.74 | 7.9e−05 |
| 214241_at | NDUFB8 | 1.67 | 5.7e−05 |
| 203371_s_at | NDUFB3 | 1.51 | 0.002 |
| 218226_s_at | NDUFB4 | 1.49 | 0.003 |
| 202001_s_at | NDUFA6 | 1.37 | 0.02 |
| 218160_at | NDUFA8 | 1.31 | 0.04 |
| 202785_at | NDUFA7 | 1.31 | 0.04 |
| 218563_at | NDUFA3 | 1.30 | 0.04 |
| Complex II (1 probe) | | | |
| 214166_at | SDHB | 1.40 | 0.009 |
| Complex III (2 probes) | | | |
| 207618_s_at | BCS1L | 1.76 | 7.1e−06 |
| 202233_s_at | UQCR8 | 1.51 | 0.001 |
| Complex IV (10 probes) | | | |
| 213736_at | COX5B | 2.14 | 1.4e−08 |
| 218057_x_at | COX4NB | 1.94 | 7.7e−07 |
| 201754_at | COX6C | 1.74 | 7.1e−05 |
| 201441_at | COX6B1 | 1.67 | 0.0001 |
| 200925_at | COX6A1 | 1.64 | 8.8e−05 |
| 203880_at | COX17 | 1.60 | 0.0003 |
| 217451_at | COX5A | 1.49 | 0.006 |
| 202110_at | COX7B | 1.42 | 0.01 |
| 217249_x_at | COX7A2 | 1.33 | 0.035 |
| 216003_at | COX10 | 1.33 | 0.046 |
| Complex V (13 probes) | | | |
| 221677_s_at | ATP5O | 2.22 | 2.1e−10 |
| 207552_at | ATP5G2 | 1.90 | 7.5e−06 |
| 207335_x_at | ATP5I | 1.84 | 8.4e−06 |
| 217801_at | ATP5E | 1.64 | 0.0002 |

TABLE 5-continued

Prognostic value of mitochondrial markers in gastric cancers.

| Gene Probe ID | Symbol | Hazard-Ratio | Log-Rank Test |
|---|---|---|---|
| 208972_s_at | ATP5G1 | 1.51 | 0.002 |
| 210149_s_at | ATP5H | 1.49 | 0.003 |
| 202961_s_at | ATP5J2 | 1.47 | 0.004 |
| 210453_x_at | ATP5L | 1.45 | 0.006 |
| 207573_x_at | ATP5L | 1.44 | 0.01 |
| 208746_x_at | ATP5L | 1.40 | 0.009 |
| 213366_x_at | ATP5C | 1.33 | 0.03 |
| 206993_at | ATP5S | 1.29 | 0.04 |
| 213366_x_at | ATP5C1 | 1.33 | 0.03 |

TABLE 6

Exemplary compact gastric cancer Mito-Signature for predicting clinical outcome.

| Gene Probe ID | Symbol | Hazard-Ratio | Log-Rank Test |
|---|---|---|---|
| 201757_at | NDUFS5 | 2.27 | 6e−10 |
| 208844_at | VDAC3 | 2.22 | 1.4e−09 |
| 221677_s_at | ATP5O | 2.22 | 2.1e−10 |
| 200955_at | IMMT | 2.20 | 2.4e−09 |
| 204599_s_at | MRPL28 | 2.17 | 1.2e−08 |
| 213736_at | COX5B | 2.14 | 1.4e−08 |
| 221997_s_at | MRPL52 | 2.12 | 3.2e−09 |
| 208694_at | PRKDC | 2.05 | 1.2e−07 |
| Combined | | 2.77 | 1.4e−14 |

In some embodiments, the mitochondrial markers may include mitochondrial proteins, RNA, and/or DNA that are upregulated or increased in ovarian cancers. Table 7, adapted from U.S. Provisional Application No. 62/508,788, the contents of which is incorporated by reference in its entirety, shows exemplary proteins that may be used as mitochondrial biomarkers in ovarian cancers. As is shown in Table 7, mitochondrial biomarkers may include mitochondrial proteins, RNA, and/or DNA associated with heat shock proteins and chaperones, membrane proteins, mitochondrial antioxidants, mitochondrial creatine kinases, large and/or small ribosomal subunits, and OXPHOS complexes. Exemplary Mito-Signatures for ovarian cancer are shown in Table 8.

TABLE 7

Prognostic value of mitochondrial markers in ovarian cancers.

| Gene Probe ID | Symbol | Hazard-Ratio | Log-Rank Test |
|---|---|---|---|
| Chaperones/HSPs | | | |
| 200691_s_at | HSPA9 | 1.77 | 0.047 |
| Membrane Proteins | | | |
| 200955_at | IMMT | 2.61 | 0.002 |
| 218408_at | TIMM10 | 2.63 | 0.0008 |
| 201821_s_at | TIMM17A | 2.46 | 0.003 |
| 217981_s_at | TIMM10B | 1.94 | 0.05 |
| 218118_s_at | TIMM23 | 1.79 | 0.05 |
| 201519_at | TOMM70A | 2.28 | 0.005 |
| 211662_s_at | VDAC2 | 2.32 | 0.01 |
| 208845_at | VDAC3 | 2.07 | 0.01 |
| 208846_s_at | VDAC3 | 1.96 | 0.048 |
| 200657_at | SLC25A5 | 2.67 | 0.0008 |
| 221020_s_at | SLC25A32 | 1.98 | 0.05 |
| Anti-Oxidant Proteins | | | |
| 201468_s_at | NQO1 | 3.48 | 0.001 |
| 210519_s_at | NQO1 | 2.37 | 0.006 |
| 215223_s_at | SOD2 | 1.82 | 0.048 |

TABLE 7-continued

Prognostic value of mitochondrial markers in ovarian cancers.

| Gene Probe ID | Symbol | Hazard-Ratio | Log-Rank Test |
|---|---|---|---|
| Mitochondrial Creatine Kinase | | | |
| 205295_at | CKMT2 | 2.27 | 0.0035 |
| Large Ribosomal Subunit | | | |
| 201717_at | MRPL49 | 3.56 | 4.3e−05 |
| 221692_s_at | MRPL34 | 2.99 | 0.001 |
| 218890_x_at | MRPL35 | 2.48 | 0.002 |
| 213897_s_at | MRPL23 | 2.48 | 0.01 |
| 217907_at | MRPL18 | 2.36 | 0.006 |
| 218281_at | MRPL48 | 2.29 | 0.007 |
| 222216_s_at | MRPL17 | 2.17 | 0.007 |
| 217980_s_at | MRPL16 | 2.17 | 0.008 |
| 219162_s_at | MRPL11 | 2.14 | 0.02 |
| 218105_s_at | MRPL4 | 1.90 | 0.03 |
| Small Ribosomal Subunit | | | |
| 203800_s_at | MRPS14 | 2.97 | 0.0002 |
| 204331_s_at | MRPS12 | 2.90 | 9e−04 |
| 210008_s_at | MRPS12 | 2.46 | 0.0035 |
| 221688_s_at | MRPS4 | 2.88 | 0.002 |
| 219819_s_at | MRPS28 | 2.64 | 0.0008 |
| 218001_at | MRPS2 | 2.15 | 0.01 |
| 219220_x_at | MRPS22 | 2.13 | 0.025 |
| 218654_s_at | MRPS33 | 2.05 | 0.02 |
| 217942_at | MRPS35 | 2.05 | 0.03 |
| 212604_at | MRPS31 | 2.02 | 0.02 |
| 221437_s_at | MRPS15 | 1.88 | 0.05 |
| Complex I | | | |
| 218563_at | NDUFA3 | 3.55 | 2.3e−05 |
| 218320_s_at | NDUFB11 | 3.12 | 7e−05 |
| 201740_at | NDUFS3 | 2.93 | 0.001 |
| 218200_s_at | NDUFB2 | 2.60 | 0.001 |
| 203371_s_at | NDUFB3 | 2.56 | 0.0008 |
| 203189_s_at | NDUFS8 | 2.43 | 0.002 |
| 218201_at | NDUFB2 | 2.43 | 0.002 |
| 203613_s_at | NDUFB6 | 2.43 | 0.008 |
| 202000_at | NDUFA6 | 2.43 | 0.0015 |
| 202785_at | NDUFA7 | 2.30 | 0.01 |
| 220864_s_at | NDUFA13 | 2.25 | 0.006 |
| 209303_at | NDUFS4 | 2.20 | 0.009 |
| 218160_at | NDUFA8 | 2.16 | 0.008 |
| 203190_at | NDUFS8 | 2.15 | 0.01 |
| 202941_at | NDUFV2 | 2.13 | 0.02 |
| 208714_at | NDUFV1 | 2.07 | 0.03 |
| 209224_s_at | NDUFA2 | 2.03 | 0.044 |
| 211752_s_at | NDUFS7 | 1.98 | 0.02 |
| 217860_at | NDUFA10 | 1.95 | 0.037 |
| 202298_at | NDUFA1 | 1.91 | 0.03 |
| 208969_at | NDUFA9 | 1.89 | 0.26 |
| 201966_at | NDUFS2 | 1.86 | 0.035 |
| Complex II | | | |
| 210131_x_at | SDHC | 2.97 | 0.0005 |
| 202004_x_at | SDHC | 2.78 | 0.0005 |
| 202675_at | SDHB | 1.83 | 0.04 |
| Complex III | | | |
| 208909_at | UQCRFS1 | 3.68 | 9.8e−05 |
| 201568_at | UQCR7 | 2.28 | 0.004 |
| 209065_at | UQCR6 | 2.12 | 0.04 |
| 202090_s_at | UQCR | 1.86 | 0.04 |
| 212600_s_at | UQCR2 | 1.76 | 0.047 |
| Complex IV | | | |
| 201441_at | COX6B | 2.64 | 0.0009 |
| 203880_at | COX17 | 2.49 | 0.004 |
| 203858_s_at | COX10 | 2.47 | 0.002 |
| 211025_x_at | COX5B | 2.34 | 0.004 |
| 202343_x_at | COX5B | 2.32 | 0.004 |
| 202110_at | COX7B | 2.30 | 0.02 |
| 218057_x_at | COX4NB | 2.08 | 0.01 |
| 202698_x_at | COX4I1 | 1.89 | 0.03 |
| 201119_s_at | COX8A | 1.87 | 0.04 |
| 204570_at | COX7A | 1.76 | 0.05 |

TABLE 7-continued

Prognostic value of mitochondrial markers in ovarian cancers.

| Gene Probe ID | Symbol | Hazard-Ratio | Log-Rank Test |
|---|---|---|---|
| Complex V | | | |
| 208870_x_at | ATP5C | 2.57 | 0.0008 |
| 213366_x_at | ATP5C | 2.44 | 0.002 |
| 205711_x_at | ATP5C | 2.08 | 0.01 |
| 207507_s_at | ATP5G3 | 2.40 | 0.002 |
| 210453_x_at | ATP5L | 2.35 | 0.003 |
| 208746_x_at | ATP5L | 2.24 | 0.005 |
| 207573_x_at | ATP5L | 2.20 | 0.006 |
| 208972_s_at | ATP5G | 2.15 | 0.007 |
| 207508_at | ATP5G3 | 2.12 | 0.01 |
| 202961_s_at | ATP5J2 | 1.91 | 0.02 |
| 217848_s_at | PPA1 | 1.89 | 0.03 |
| 202325_s_at | ATP5J | 1.78 | 0.05 |

TABLE 8

Exemplary compact ovarian cancer Mito-Signatures for predicting clinical outcome.

| Gene Probe ID | Symbol | Hazard-Ratio | Log-Rank Test |
|---|---|---|---|
| Mito-Signature 1 | | | |
| 208909_at | UQCRFS1 | 3.68 | 9.8e−05 |
| 201717_at | MRPL49 | 3.56 | 4.3e−05 |
| Combination | | 4.59 | 3.1e−05 |
| Mito-Signature 2 | | | |
| 208909_at | UQCRFS1 | 3.68 | 9.8e−05 |
| 218563_at | NDUFA3 | 3.55 | 2.3e−05 |
| Combination | | 5.03 | 1.2e−05 |
| Mito-Signature 3 | | | |
| 208909_at | UQCRFS1 | 3.68 | 9.8e−05 |
| 218563_at | NDUFA3 | 3.55 | 2.3e−05 |
| 201202_at | PCNA | 2.85 | 0.0003 |
| Combination | | 5.63 | 7.6e−06 |

In some embodiments, the mitochondrial markers may include mitochondrial proteins, RNA, and/or DNA that are upregulated or increased in breast cancers. Table 9, adapted from U.S. Provisional Application No. 62/508,750, the contents of which is incorporated by reference in its entirety, shows exemplary proteins that may be used as mitochondrial biomarkers in breast cancers. As is shown in Table 9, mitochondrial biomarkers may include mitochondrial proteins, RNA, and/or DNA associated mitochondrial chaperones, membrane proteins, mitochondrial carrier families, mitochondrial antioxidants, mitochondrial creatine kinases, large and/or small ribosomal subunits, and OXPHOS complexes. Exemplary Mito-Signatures for breast cancer are shown in Table 10.

TABLE 9

Prognostic value of mitochondrial markers in breast cancers.

| Gene Probe ID | Symbol | Hazard-Ratio | Log-Rank Test |
|---|---|---|---|
| Mito Chaperones | | | |
| 200807_s_at | HSPD1 | 3.61 | 5.9e−06 |
| 200806_s_at | HSPD1 | 2.30 | 0.006 |
| 200691_s_at | HSPA9 | 2.04 | 0.01 |
| 205565_s_at | FXN | 1.83 | 0.038 |
| 221235_s_at | TRAP1 | 1.79 | 0.047 |
| Mito Membrane Proteins | | | |
| 211662_s_at | VDAC2 | 4.17 | 2.2e−07 |
| 210626_at | AKAP1 | 2.15 | 0.01 |
| 200955_at | IMMT | 1.81 | 0.04 |
| 201519_at | TOMM70A | 2.78 | 0.0003 |
| 201512_s_at | TOMM70A | 2.15 | 0.01 |
| 203093_s_at | TIMM44 | 2.23 | 0.01 |
| 218188_s_at | TIMM13 | 2.23 | 0.02 |
| 201822_at | TIMM17A | 2.01 | 0.01 |
| 215171_s_at | TIMM17A | 1.85 | 0.04 |
| 203342_at | TIMM17B | 1.78 | 0.04 |
| Mito Carrier Family | | | |
| 217961_at | SLC25A38 | 2.77 | 0.0003 |
| 210010_s_at | SLC25A1 | 2.38 | 0.002 |
| 200657_at | SLC25A5 | 2.04 | 0.01 |
| 221020_s_at | SLC25A32 | 1.98 | 0.02 |
| Mito Anti-Oxidants | | | |
| 215223_s_at | SOD2 | 2.94 | 0.0001 |
| 215078_at | SOD2 | 2.81 | 0.008 |
| Mito Creatine Kinase | | | |
| 205295_at | CKMT2 | 2.18 | 0.04 |
| 202712_s_at | CKMT1A | 2.03 | 0.02 |
| Large Ribosomal Subunit | | | |
| 218027_at | MRPL15 | 3.28 | 1.6e−05 |
| 217907_at | MRPL18 | 2.91 | 0.0001 |
| 219244_s_at | MRPL46 | 2.89 | 0.02 |
| 218270_at | MRPL24 | 2.38 | 0.002 |
| 218049_s_at | MRPL13 | 2.14 | 0.01 |
| 218281_at | MRPL48 | 2.11 | 0.01 |
| 208787_at | MRPL3 | 2.07 | 0.03 |
| 213897_s_at | MRPL23 | 2.02 | 0.04 |
| 218105_s_at | MRPL4 | 1.99 | 0.02 |
| 222216_s_at | MRPL17 | 1.97 | 0.02 |
| 217919_s_at | MRPL42 | 1.88 | 0.05 |
| 218202_x_at | MRPL44 | 1.78 | 0.04 |
| Small Ribosomal Subunit | | | |
| 204330_s_at | MRPS12 | 2.35 | 0.03 |
| 211595_s_at | MRPS11 | 2.26 | 0.01 |
| 219819_s_at | MRPS28 | 1.88 | 0.03 |
| 217919_s_at | MRPL42 | 1.88 | 0.05 |
| 219220_x_at | MRPS22 | 1.85 | 0.04 |
| 218654_s_at | MRPS33 | 1.84 | 0.04 |
| Complex I | | | |
| 218160_at | NDUFA8 | 2.45 | 0.002 |
| 202000_at | NDUFA6 | 2.41 | 0.002 |
| 202001_s_at | NDUFA6 | 2.23 | 0.006 |
| 203039_s_at | NDUFS1 | 2.40 | 0.003 |
| 201740_at | NDUFS3 | 2.17 | 0.006 |
| 203613_s_at | NDUFB6 | 1.99 | 0.02 |
| 208714_at | NDUFV1 | 1.96 | 0.03 |
| 203606_at | NDUFS6 | 1.92 | 0.04 |
| 202298_at | NDUFA1 | 1.89 | 0.03 |
| Complex III | | | |
| 209065_at | UQCRB | 3.42 | 1.9e−05 |
| 209066_x_at | UQCRB | 2.12 | 0.01 |
| 205849_s_at | UQCR6 | 2.53 | 0.002 |
| 201066_at | UQCR4 | 1.96 | 0.02 |
| 212600_s_at | UQCRC2 | 1.92 | 0.04 |
| Complex IV | | | |
| 203880_at | COX17 | 2.99 | 7.6e−05 |
| 213735_s_at | COX5B | 2.51 | 0.001 |
| 202343_x_at | COX5B | 2.10 | 0.01 |
| 211025_x_at | COX5B | 2.08 | 0.01 |
| 202698_x_at | COX4I1 | 2.36 | 0.02 |
| 200925_at | COX6A1 | 2.14 | 0.01 |
| 218057_x_at | COX4NB | 1.99 | 0.04 |
| 217249_x_at | COX7A2 | 1.90 | 0.03 |

TABLE 9-continued

Prognostic value of mitochondrial markers in breast cancers.

| Gene Probe ID | Symbol | Hazard-Ratio | Log-Rank Test |
|---|---|---|---|
| Complex V | | | |
| 202325_s_at | ATP5J | 2.65 | 0.01 |
| 202961_s_at | ATP5J2 | 2.44 | 0.035 |
| 213366_x_at | ATP5C1 | 2.19 | 0.01 |
| 208870_x_at | ATP5C1 | 2.08 | 0.01 |
| 205711_x_at | ATP5C1 | 2.00 | 0.02 |
| 217848_s_at | PPA1 | 2.07 | 0.01 |
| 221677_s_at | ATP5O | 2.03 | 0.02 |
| 217801_at | ATP5E | 1.99 | 0.02 |
| 207508_at | ATP5G3 | 1.93 | 0.02 |

TABLE 10

Exemplary compact breast cancer Mito-Signatures for predicting clinical outcome.

| Gene Probe ID | Symbol | Hazard-Ratio | Log-Rank Test |
|---|---|---|---|
| Mito-Signature 1 | | | |
| 200807_s_at | HSPD1 | 3.61 | 5.9e−06 |
| 209065_at | UQCRB | 3.42 | 1.9e−05 |
| 218027_at | MRPL15 | 3.28 | 1.6e−05 |
| 203880_at | COX17 | 2.99 | 7.6e−05 |
| Combined | | 5.34 | 1e−09 |
| Mito-Signature 2 | | | |
| 211662_s_at | VDAC2 | 4.17 | 2.2e−07 |
| 200807_s_at | HSPD1 | 3.61 | 5.9e−06 |
| Combined | | 5.19 | 6e−09 |

In some embodiments, the mitochondrial markers may include mitochondrial proteins, RNA, and/or DNA that are upregulated or increased in lung cancers. Table 11, adapted from U.S. Provisional Application No. 62/508,769, the contents of which is incorporated by reference in its entirety, shows exemplary proteins that may be used as mitochondrial biomarkers in lung cancers. As is shown in Table 11, mitochondrial biomarkers may include mitochondrial proteins, RNA, and/or DNA associated with mitochondrial heat shock proteins and membrane proteins, mitochondrial creatine kinases, mitochondrial genome maintenance proteins, large and/or small ribosomal subunits, and OXPHOS complexes.

TABLE 11

Prognostic value of mitochondrial markers in lung cancers.

| Gene Probe ID | Symbol | Hazard-Ratio | Log-Rank Test |
|---|---|---|---|
| HSPs and Membrane Proteins (28 probes in total) | | | |
| 200806_s_at | HSPD1 | 4.89 | <1.0e−16 |
| 218119_at | TIMM23 | 4.68 | 1.1e−16 |
| 218357_s_at | TIMM8B | 4.26 | 7.8e−16 |
| 203342_at | TIMM17B | 3.31 | 2.5e−11 |
| 203093_s_at | TIMM44 | 2.29 | 1.1e−09 |
| 217981_s_at | TIMM10B | 2.15 | 1.2e−06 |
| 218316_at | TIMM9 | 2.06 | 4.3e−08 |
| 201821_s_at | TIMM17A | 2.04 | 1.7e−09 |
| 218188_s_at | TIMM13 | 1.94 | 8.5e−09 |
| 218118_s_at | TIMM23 | 1.83 | 1.8e−07 |
| 218408_at | TIMM10 | 1.79 | 4e−07 |
| 202264_s_at | TOMM40 | 4.29 | 1.1e−14 |
| 217960_s_at | TOMM22 | 3.19 | 1.3e−13 |
| 201870_at | TOMM34 | 2.83 | 9.8e−12 |
| 201812_s_at | TOMM7 | 2.84 | 5.4e−13 |

TABLE 11-continued

Prognostic value of mitochondrial markers in lung cancers.

| Gene Probe ID | Symbol | Hazard-Ratio | Log-Rank Test |
|---|---|---|---|
| 201512_s_at | TOMM70A | 1.90 | 3.1e−08 |
| 212773_s_at | TOMM20 | 1.54 | 0.0006 |
| 217139_at | VDAC1 | 3.74 | 1.9e−14 |
| 217140_s_at | VDAC1 | 2.58 | 1.1e−16 |
| 212038_s_at | VDAC1 | 1.63 | 7.8e−05 |
| 208844_at | VDAC3 | 3.64 | 3.9e−14 |
| 211662_s_at | VDAC2 | 2.36 | 6e−14 |
| 210625_s_at | AKAP1 | 1.88 | 1.3e−06 |
| 200657_at | SLC25A5 | 1.54 | 0.0001 |
| Mitochondrial Creatine Kinase (2 probes in total) | | | |
| 202712_s_at | CKMT1A | 2.88 | 7.8e−10 |
| 205295_at | CKMT2 | 1.51 | 0.0005 |
| Mitochondrial Genome Maintenance (3 probes in total) | | | |
| 210543_s_at | PRKDC | 4.69 | 1.1e−16 |
| 208694_at | PRKDC | 2.23 | 4.3e−12 |
| 215757_at | PRKDC | 1.65 | 4.0e−05 |
| Large Ribosomal Subunit (21 probes in total) | | | |
| 218281_at | MRPL48 | 4.36 | 1.9e−15 |
| 213897_s_at | MRPL23 | 3.55 | 5.4e−13 |
| 219162_s_at | MRPL11 | 3.29 | 2.5e−13 |
| 221997_s_at | MRPL52 | 3.20 | 3.6e−14 |
| 221692_s_at | MRPL34 | 3.08 | 1.6e−11 |
| 203931_s_at | MRPL12 | 2.82 | 3.3e−12 |
| 218887_at | MRPL2 | 2.81 | 4.4e−11 |
| 217919_s_at | MRPL42 | 2.54 | 1.6e−13 |
| 218270_at | MRPL24 | 2.35 | 1.8e−09 |
| 218105_s_at | MRPL4 | 2.32 | 1.6e−09 |
| 218202_x_at | MRPL44 | 2.19 | 2.5e−10 |
| 222216_s_at | MRPL17 | 2.02 | 1.4e−08 |
| 218890_x_at | MRPL35 | 1.96 | 5.7e−09 |
| 204599_s_at | MRPL28 | 1.91 | 1.4e−07 |
| 220527_at | MRPL20 | 1.84 | 9.1e−05 |
| 201717_at | MRPL49 | 1.68 | 8.7e−06 |
| 218049_s_at | MRPL13 | 1.68 | 8.1e−06 |
| 217980_s_at | MRPL16 | 1.66 | 1.5e−05 |
| 203152_at | MRPL40 | 1.62 | 0.0001 |
| 218027_at | MRPL15 | 1.59 | 0.0001 |
| 203781_at | MRPL33 | 1.47 | 0.001 |
| Small Ribosomal Subunit (19 probes in total) | | | |
| 204331_s_at | MRPS12 | 4.10 | 1.1e−16 |
| 210008_s_at | MRPS12 | 3.93 | 4.9e−14 |
| 204330_s_at | MRPS12 | 3.27 | 1e−13 |
| 213840_s_at | MRPS12 | 2.99 | 2.3e−12 |
| 217932_at | MRPS7 | 3.55 | 2.3e−12 |
| 218001_at | MRPS2 | 3.28 | 1e−11 |
| 221688_s_at | MRPS4 | 3.09 | 7.7e−11 |
| 211595_s_at | MRPS11 | 2.96 | 9.1e−12 |
| 215919_s_at | MRPS11 | 1.55 | 0.0002 |
| 218112_at | MRPS34 | 2.43 | 7.6e−08 |
| 212604_at | MRPS31 | 2.29 | 2.7e−07 |
| 219819_s_at | MRPS28 | 1.74 | 2.7e−06 |
| 217942_at | MRPS35 | 1.70 | 8.4e−06 |
| 221437_s_at | MRPS15 | 1.59 | 0.0001 |
| 12145_at | MRPS27 | 1.61 | 7.4e−05 |
| 218398_at | MRPS30 | 1.47 | 0.003 |
| 218654_s_at | MRPS33 | 1.35 | 0.01 |
| 203800_s_at | MRPS14 | 1.27 | 0.05 |
| Complex I (27 probes in total) | | | |
| 203371_s_at | NDUFB3 | 4.30 | 3.6e−15 |
| 203189_s_at | NDUFS8 | 4.15 | 4.4e−16 |
| 203190_at | NDUFS8 | 2.94 | 2.1e−11 |
| 209303_at | NDUFS4 | 3.83 | 1.1e−15 |
| 218484_at | NDUFA4L2 | 3.33 | 2.1e−13 |
| 218226_s_at | NDUFB4 | 3.21 | 1.8e−14 |
| 220864_s_at | NDUFA13 | 3.00 | 9.5e−11 |
| 202941_at | NDUFV2 | 3.00 | 1.3e−13 |
| 201740_at | NDUFS3 | 2.92 | 1.2e−11 |
| 217860_at | NDUFA10 | 2.77 | 3e−14 |
| 218563_at | NDUFA3 | 2.23 | 1.9e−10 |
| 214241_at | NDUFB8 | 2.23 | 1.5e−09 |
| 218201_at | NDUFB2 | 2.21 | 1.2e−08 |

TABLE 11-continued

Prognostic value of mitochondrial markers in lung cancers.

| Gene Probe ID | Symbol | Hazard-Ratio | Log-Rank Test |
|---|---|---|---|
| 215850_s_at | NDUFA5 | 1.83 | 3.6e−07 |
| 202785_at | NDUFA7 | 1.81 | 3e−07 |
| 202298_at | NDUFA1 | 1.72 | 3e−06 |
| 201966_at | NDUFS2 | 1.70 | 6.6e−06 |
| 202839_s_at | NDUFB7 | 1.64 | 0.0009 |
| 201757_at | NDUFS5 | 1.64 | 4.3e−05 |
| 209224_s_at | NDUFA2 | 1.59 | 6.6e−05 |
| 208969_at | NDUFA9 | 1.56 | 0.0002 |
| 211752_s_at | NDUFS7 | 1.50 | 0.0007 |
| 203613_s_at | NDUFB6 | 1.49 | 0.0009 |
| 209223_at | NDUFA2 | 1.49 | 0.0009 |
| 218320_s_at | NDUFB11 | 1.48 | 0.001 |
| 218200_s_at | NDUFB2 | 1.48 | 0.001 |
| 208714_at | NDUFV1 | 1.44 | 0.002 |
| Complex II (5 probes in total) | | | |
| 216591_s_at | SDHC | 4.27 | 7.8e−16 |
| 202004_x_at | SDHC | 3.64 | 4e−14 |
| 210131_x_at | SDHC | 3.45 | 4.2e−14 |
| 202675_at | SDHB | 2.06 | 7.4e−07 |
| 214166_at | SDHB | 1.94 | 2.5e−08 |
| Complex III (8 probes in total) | | | |
| 201568_at | UQCR7 | 3.34 | 3.7e−13 |
| 209066_x_at | UQCR6 | 2.96 | 2.5e−10 |
| 202233_s_at | UQCR8 | 2.09 | 5.9e−07 |
| 208909_at | UQCRFS1 | 1.69 | 2.6e−05 |
| 201066_at | UQCR4/CYC1 | 1.54 | 0.0006 |
| 207618_s_at | BCS1L | 1.54 | 0.0003 |
| 205849_s_at | UQCR6 | 1.48 | 0.0008 |
| 202090_s_at | UQCR | 1.45 | 0.004 |
| Complex IV (19 probes in total) | | | |
| 211025_x_at | COX5B | 4.46 | 5.3e−15 |
| 202343_x_at | COX5B | 3.97 | 1.1e−16 |
| 213735_s_at | COX5B | 2.15 | 9.6e−10 |
| 213736_at | COX5B | 1.51 | 0.0015 |
| 200925_at | COX6A | 3.94 | 1.1e−16 |
| 201119_s_at | COX8A | 3.78 | 2.4e−15 |
| 203880_at | COX17 | 3.55 | 3.9e−15 |
| 201754_at | COX6C | 3.24 | 1.8e−14 |
| 217249_x_at | COX7A2 | 3.05 | 3.3e−13 |
| 201441_at | COX6B | 2.93 | 3.8e−12 |
| 206353_at | COX6A2 | 2.77 | 1.8e−11 |
| 203858_s_at | COX10 | 2.44 | 1.3e−09 |
| 202110_at | COX7B | 2.29 | 2.5e−12 |
| 216003_at | COX10 | 2.18 | 1.8e−07 |
| 221550_at | COX15 | 2.09 | 1.5e−10 |
| 217451_at | COX5A | 2.01 | 9e−06 |
| 218057_x_at | COX4NB | 1.54 | 0.0008 |
| 204570_at | COX7A | 1.51 | 0.0015 |
| 202698_x_at | COX4I1 | 1.39 | 0.01 |
| Complex V (23 probes in total) | | | |
| 202961_s_at | ATP5J2 | 4.38 | 1.3e−14 |
| 207507_at | ATP5G3 | 4.14 | <1e−17 |
| 207508_at | ATP5G3 | 2.34 | 1.6e−13 |
| 210149_s_at | ATP5H | 3.70 | 3.7e−15 |
| 209492_x_at | ATP5I | 3.33 | 7.7e−13 |
| 207335_x_at | ATP5I | 2.14 | 2e−08 |
| 203926_x_at | ATP5D | 3.02 | 2.7e−11 |
| 213041_s_at | ATP5D | 2.41 | 3.1e−10 |
| 208764_s_at | ATP5G2 | 2.75 | 2.9e−10 |
| 207552_at | ATP5G2 | 2.55 | 4.3e−09 |
| 217368_at | ATP5G2 | 1.85 | 4.9e−07 |
| 217801_at | ATP5E | 2.62 | 2e−09 |
| 210453_x_at | ATP5L | 2.56 | 1.8e−11 |
| 207573_x_at | ATP5L | 2.25 | 1.9e−10 |
| 208746_x_at | ATP5L | 2.10 | 7.4e−10 |
| 201322_at | ATP5B | 1.88 | 1.5e−07 |
| 206992_s_at | ATP5S | 1.88 | 2.9e−07 |
| 206993_at | ATP5S | 1.85 | 2.1e−07 |
| 208972_s_at | ATP5G | 1.87 | 5.4e−08 |
| 221677_s_at | ATP5O | 1.71 | 6.8e−06 |
| 208870_x_at | ATP5C | 1.54 | 0.0008 |
| 205711_x_at | ATP5C | 1.42 | 0.004 |
| 213366_x_at | ATP5C | 1.40 | 0.007 |

The present disclosure also relates to methods of treating a neoplastic disease in a patient. Such treatment may occur following the determination of increased expression levels of one or more mitochondrial markers. Methods may include obtaining a sample of a neoplasm from a neoplastic disease patient, determining the expression level of one or more mitochondrial markers in the CSCs (e.g., Mito-signature) of the neoplasm sample relative to a control sample, and, if the higher expression levels of one or more mitochondrial markers is detected, administering to the patient a therapeutically effective amount of an anti-mitochondrial agent. The anti-mitochondrial agent may include one or more mitoriboscins, mitoketoscins, and/or antimitoscins. The anti-mitochondrial agent may include compounds that inhibit mitochondrial function as an off-target effect, such as metformin, tetracycline family members (such as doxycycline), erythromycin family members (such as azithromycin), atovaquone, bedaquiline. In some embodiments, the anti-mitochondrial agent comprises a lactate transporter inhibitor or a glycolysis inhibitor. In some embodiments, the glycolysis inhibitor comprises an agent which inhibits triose-phosphate isomerase, fructose 1,6 bisphosphate aldolase, glycero-3-phosphate dehydrogenase, phosphoglycerate kinase, phosphoglycerate mutase, enolase, pyruvate kinase, and/or lactate dehydrogenase.

In some embodiments, the neoplastic disease is a breast neoplasm subtype such as ER(+), PR(+), HER2(+), triple-negative (ER(−)/PR(−)/HER2(−)), ER(−), PR(−), any neoplasm and nodal stages, and any neoplasm grades. The neoplasm may include Luminal A, Luminal B, and Basal breast cancers. In some embodiments, wherein the neoplasm is a pre-malignant lesion such as a ductal carcinoma in situ (DCIS) of the breast or myelodysplastic syndrome of the bone marrow. In some embodiments, the neoplasm may be from a tissue including breast, skin, kidney, lung, pancreas, gastric, rectum and colon, prostate, ovarian, and bladder, and may include epithelial cells, non-epithelial cells, lymphomas, sarcomas, and melanomas.

Figure 9:
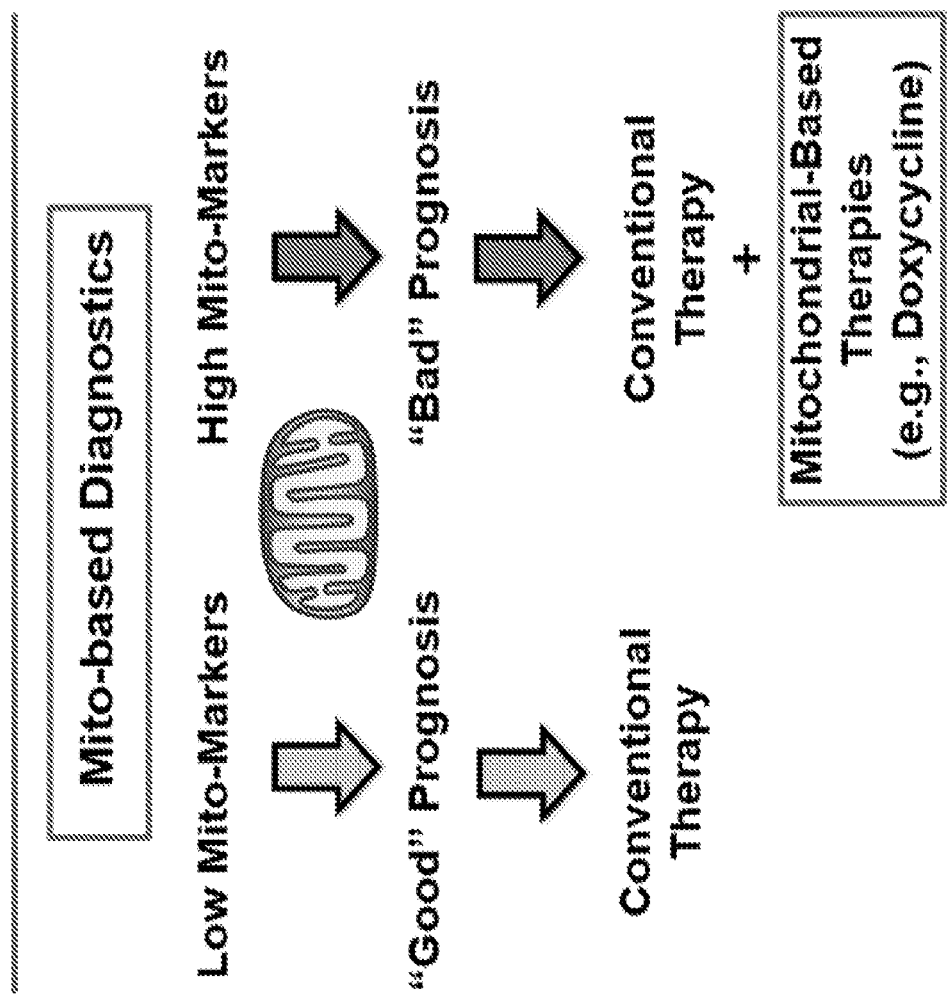
FIG. 9 provides a summary for personalized cancer diagnosis and treatment based on mitochondrial-based diagnostics.

In some embodiments, a patient may be treated with an anti-mitochondrial agent concurrently with an anti-angiogenic agent and/or an anti-neoplastic agent. For example, patients may be treated with an anti-mitochondrial agent in addition to treatment with a conventional cancer therapy, as is outline in FIG. 9. In some embodiments, one or more anti-neoplastic agents and/or anti-angiogenic agents may be administered simultaneously to or sequentially with the anti-mitochondrial agent. Anti-angiogenic agents may include one or more of angiostatin, bevacizumab, arresten, canstatin, combretastatin, endostatin, NM-3, thrombospondin, tumstatin, 2-methoxyestradiol, Vitaxin, Getfitinib, ZD6474, erlotinib, CI1033, PKI1666, cetuximab, PTK787, SU6668, SU1 1248, trastuzumab, Marimastat, COL-3, Neovastat, 2-ME, SU6668, anti-VEGF antibody, Medi-522 (Vitaxin E), tumstatin, arrestin, recombinant EPO, troponin I, EMD121974, IFN-α celecoxib, PD0332991, tamoxifen, paclitaxel (taxol) and thalidomide. Anti-neoplastic agents may include natural products such as vitamin C, caffeic acid phenyl ester (CAPE), and/or berberine. The anti-neoplastic agent may include one or more of 17-AAG, Apatinib, Ascomycin, Axitinib, Bexarotene, Bortezomib, Bosutinib, Bryostatin 1, Bryostatin 2, Canertinib, Carboplatin, Cediranib, Cisplatin, Cyclopamine, Dasatinib, 17-DMAG, Docetaxel, Doramapimod, Dovitinib, Erlotinib, Everolimus, Gefitinib, Geldanamycin, Gemcitabine, Imatinib, Imiquimod, Ingenol 3-Angelate, Ingenol 3-Angelate 20-Acetate, Irinotecan, Lapatinib, Lestaurtinib, Nedaplatin, Masitinib, Mubritinib, Nilotinib, NVP-BEZ235, OSU-03012, Oxaliplatin, Paclitaxel, Palbociclib (and other CDK4/6 inhibitors), Pazopanib, Picoplatin, Pimecrolimus, PKC412, Rapamycin, Satraplatin, Sorafenib, Sunitinib, Tandutinib, Tivozanib, Thalidomide, Temsirolimus, Tozasertib, Vandetanib, Vargatef, Vatalanib, Zotarolimus, ZSTK474, Bevacizumab (Avasti), Cetuximab, Herceptin, Rituximab, Tamoxifen, Trastuzumab, Apatinib, Axitinib, Bisindolylmaleimide I, Bisindolylmaleimide I, Bosutinib, Canertinib, Cediranib, Chelerythrine, CP690550, Dasatinib, Dovitinib, Erlotinib, Fasudil, Gefitinib, Genistein, Go 6976, H-89, HA-1077, Imatinib, K252a, K252c, Lapatinib, Di-p- Toluenesulfonate, Lestaurtinib, LY 294002, Masitinib, Mubritinib, Nilotinib, OSU-03012, Pazopanib, PD 98059, PKC412, Roscovitine, SB 202190, SB 203580, Sorafenib, SP600125, Staurosporine, Sunitinib, Tandutinib, Tivozanib, Tozasertib, Tyrphostin AG 490, Tyrphostin AG 1478, U0126, Vandetanib, Vargatef, Vatalanib, Wortmannin, ZSTK474, Cyclopamine, Carboplatin, Cisplatin, Eptaplatin, Nedaplatin, Oxaliplatin, Picoplatin, Satraplatin, Bortezomib (Velcade), Metformin, Halofuginone. Metformin, N-acetyl-cysteine (NAC), RTA 402 (Bardoxolone methyl), Auranofin, BMS-345541, IMD-0354, PS-1145, TPCA-I, Wedelolactone, Echinomycin, 2-deoxy-D-glucose (2-DG), 2-bromo-D-glucose, 2-fluoro-D-glucose, and 2-iodo- D-glucose, dichloro-acetate (DCA), 3-chloro-pyruvate, 3-Bromo-pyruvate (3-BrPA), 3-Bromo-2-oxopropionate, Oxamate, LY 294002, NVP-BEZ235, Rapamycin, Wortmannin, Quercetin, Resveratrol, N-acetyl-cysteine (NAC), N-acetyl-cysteine amide (NACA), Ascomycin, CP690550, Cyclosporin A, Everolimus, Fingolimod, FK-506, Mycophenolic Acid, Pimecrolimus, Rapamycin, Temsirolimus, Zotarolimus, Roscovitine, PD 0332991 (CDK4/6 inhibitor), Chloroquine, BSI-201, Olaparib, DR 2313, and NU 1025.

The present disclosure relates to diagnostic kits that may be used to assay a cancer sample for sensitivity to mitochondrial inhibitor therapy. In some embodiments, this kit or platform, known as MITO-ONC-RX, includes both therapeutic and diagnostic modalities (FIG. 12). In some embodiments, the present disclosure includes a kit for measuring one or more mitochondrial markers (companion diagnostics) to identify a high-risk cancer patient population that is most likely to benefit from anti-mitochondrial therapy. In some embodiments, the kit may include a component for measuring for measuring levels of mitochondrial marker RNA, DNA, and/or protein relative to a normal control. In some embodiments, the mitochondrial marker is measured by any number of ways known in the art for measuring RNA, DNA, and or protein, including quantitative PCR and/or RT-PCR kits, microarrays, Northern blots, and Western blots. In some embodiments, the kit may include an antibody specific to a mitochondrial marker. The antibody may be a monoclonal or a polyclonal antibody. In some embodiments, the kit may include a molecule that binds to at least one of a mitochondrial ribosomal protein (MRP), an OXPHOS complex, and a mitochondrial membrane protein/chaperone.

The terminology used in the description of the invention herein is for the purpose of describing particular embodiments only and is not intended to be limiting of the invention. As used in the description of the invention and the appended claims, the singular forms "a," "an" and "the" are intended to include the plural forms as well, unless the context clearly indicates otherwise. The invention includes numerous alternatives, modifications, and equivalents as will become apparent from consideration of the following detailed description.

It will be understood that although the terms "first," "second," "third," "a)," "b)," and "c)," etc. may be used herein to describe various elements of the invention should not be limited by these terms. These terms are only used to distinguish one element of the invention from another. Thus, a first element discussed below could be termed an element aspect, and similarly, a third without departing from the teachings of the present invention. Thus, the terms "first," "second," "third," "a)," "b)," and "c)," etc. are not intended to necessarily convey a sequence or other hierarchy to the associated elements but are used for identification purposes only. The sequence of operations (or steps) is not limited to the order presented in the claims.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other references mentioned herein are incorporated by reference in their entirety. In case of a conflict in terminology, the present specification is controlling.

Also, as used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

As used herein, the transitional phrase "consisting essentially of" (and grammatical variants) is to be interpreted as encompassing the recited materials or steps "and those that do not materially affect the basic and novel characteristic(s)" of the claimed invention. Thus, the term "consisting essentially of" as used herein should not be interpreted as equivalent to "comprising."

The term "about," as used herein when referring to a measurable value, such as, for example, an amount or concentration and the like, is meant to encompass variations of ±20%, ±10%, ±5%, ±1%, ±0.5%, or even ±0.1% of the specified amount. A range provided herein for a measurable value may include any other range and/or individual value therein.

Having thus described certain embodiments of the present invention, it is to be understood that the invention defined by the appended claims is not to be limited by particular details set forth in the above description as many apparent variations thereof are possible without departing from the spirit or scope thereof as hereinafter claimed.

What is claimed is:

1. A method for treating breast cancer in a breast cancer patient having mRNA levels of at least one of HSPD1, UQCRB, MRPL15, and COX17 mitochondrial markers exceeding a threshold level for the mitochondrial marker, the method comprising:
   obtaining a breast tumor sample obtained from a breast cancer patient having measured mRNA levels of at least one of HSPD1, UQCRB, MRPL15, and COX17 mitochondrial markers exceeding a threshold level for the mitochondrial marker;
   measuring an mRNA level of each of a plurality of mitochondrial markers in the breast tumor sample, the plurality comprising HSPD1, UQCRB, MRPL15, and COX17; and
   administering to the breast cancer patient having measured mRNA levels of at least one of the HSPD1, UQCRB, MRPL15, and COX17 mitochondrial markers exceeding a threshold level for the mitochondrial marker, a pharmaceutically effective amount of a mitochondrial inhibitor, the mitochondrial inhibitor selected from the group consisting of a mitoriboscin, a mitoketoscin, an antimitoscin, metformin, a tetracycline family member, an erythromycin family member, atovaquone, bedaquiline, and vitamin c.

2. The method of claim 1, wherein the breast tumor comprises drug-resistant stem cells, and further comprising administering to the patient at least one of an OXPHOS inhibitor, a glycolysis inhibitor, and an autophagy inhibitor.

3. The method of claim 1, wherein the at least one mitochondrial inhibitor comprises at least one of an OXPHOS inhibitor, a glycolysis inhibitor, and an autophagy inhibitor.

4. The method of claim 1, wherein the mitochondrial inhibitor is selected from the group of a tetracycline family member, a erythromycin family member, and bedaquiline.

5. The method of claim 1, wherein the mitochondrial inhibitor is doxycycline.

6. The method of claim 1, wherein the mitochondrial inhibitor is azithromycin.

7. The method of claim 4, wherein the mitochondrial inhibitor is bedaquiline.

8. The method of claim 1, wherein the mitochondrial inhibitor comprises a combination of a tetracycline family member and an erythromycin family member.

9. The method of claim 1, wherein the measuring a level of a plurality of mitochondrial markers comprises at least one of a quantitative polymerase chain reaction ("PCR") analysis, a quantitative reverse transcription ("RT")-PCR, a quantitative microarray analysis, and a Northern blot analysis.

* * * * *